(12) United States Patent
Chiang et al.

(10) Patent No.: US 8,188,262 B2
(45) Date of Patent: May 29, 2012

(54) SHORT INTERFERENCE RIBONUCLEIC ACIDS FOR TREATING ALLERGIC DISEASES

(75) Inventors: Bor-Luen Chiang, Taipei (TW); Chung-Sheng Huang, Toorak (AU)

(73) Assignee: Wholesome Biopharm Pty Ltd, Toorak, Victoria (AU)

( * ) Notice: Subject to any disclaimer, the term of this patent is extended or adjusted under 35 U.S.C. 154(b) by 105 days.

(21) Appl. No.: 12/300,337

(22) PCT Filed: May 11, 2007

(86) PCT No.: PCT/AU2007/000638
§ 371 (c)(1), (2), (4) Date: Nov. 11, 2008

(87) PCT Pub. No.: WO2007/131274
PCT Pub. Date: Nov. 22, 2007

(65) Prior Publication Data
US 2009/0264503 A1 Oct. 22, 2009

(30) Foreign Application Priority Data
May 11, 2006 (AU) .............................. 2006902491

(51) Int. Cl.
*C07H 21/00* (2006.01)
*C07H 21/02* (2006.01)

(52) U.S. Cl. ...................................... 536/24.5; 536/23.1
(58) Field of Classification Search .................... None
See application file for complete search history.

(56) References Cited

U.S. PATENT DOCUMENTS

| 2005/0182007 A1* | 8/2005 | McSwiggen et al. ........... 514/44 |
| 2005/0246794 A1 | 11/2005 | Khvorova et al. |
| 2005/0255487 A1* | 11/2005 | Khvorova et al. ................ 435/6 |
| 2005/0261219 A1* | 11/2005 | Richards et al. ................ 514/44 |

FOREIGN PATENT DOCUMENTS

| WO | WO2005033314 A | 4/2005 |
| WO | WO2005116204 | 12/2005 |

OTHER PUBLICATIONS

Popescu F D., "Antisense- and RNA interference-based therapeutic strategies in allergy".
Teixeira M.M. et al., "Chemokine-induced Eosinophil Recruitment".

* cited by examiner

*Primary Examiner* — Jennifer McDonald
(74) *Attorney, Agent, or Firm* — Thomas, Kayden, Horstemeyer & Risley, LLP

(57) ABSTRACT

Provided herein are compounds, methods and compositions for treating allergic diseases. In particular, an isolated double stranded short interfering ribonucleic acid (siRNA) with a ribonucleotide sequence complementary to at least a portion of a target gene RNA such as an airway inflammation related-gene RNA, thereby resulting in the cleavage of the expressed target gene RNA via RNA interference mechanism, and is useful as a medicament for treating allergy by alleviating or minimizing airway inflammation of a subject.

7 Claims, 24 Drawing Sheets

FIG 1
(A)
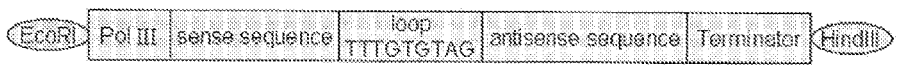
siRNA1, directed to gata-3 target sequence 316-336 :
GAAGCTCAGTATCCGCTGACG (SEQ ID NO: 1)
siRNA2, directed to gata-3 target sequence 1733-1753 :
CCACTGAATCCGGATCCCATT (SEQ ID NO: 2)
siRNA3, directed to gata-3 target sequence 1306-1324 :
GATGTCTAGCAAATCGAAA (SEQ ID NO: 3)
(B)
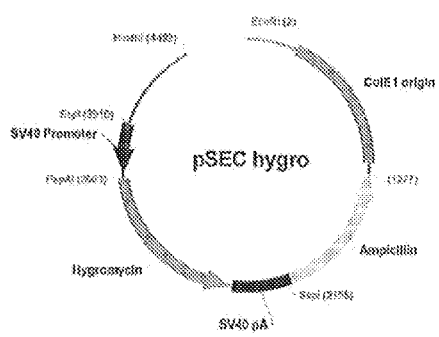
(C)
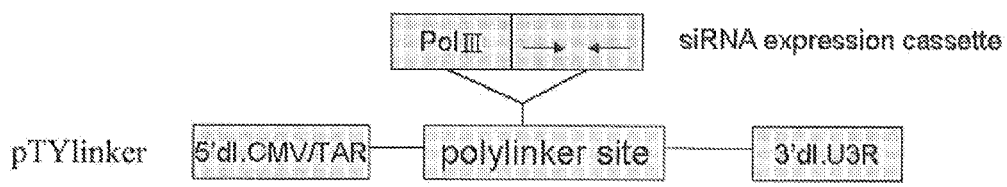

(A)

FIG 2
(B)     (a)    No pretreatment
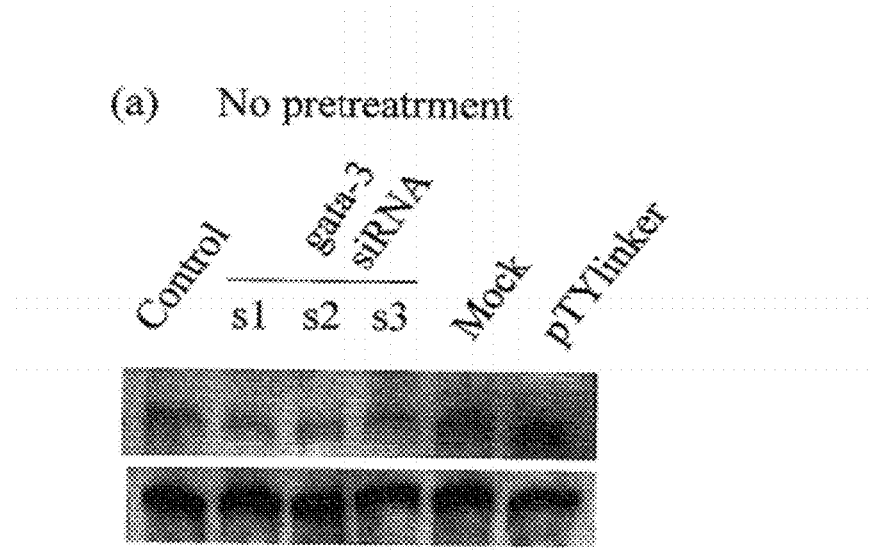
(b)    PMA 5ng/ml + cAMP 500μM
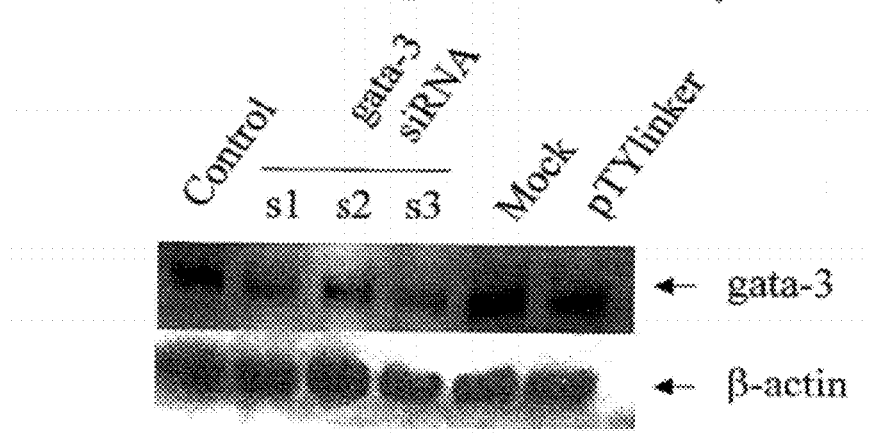

FIG 2
(C)
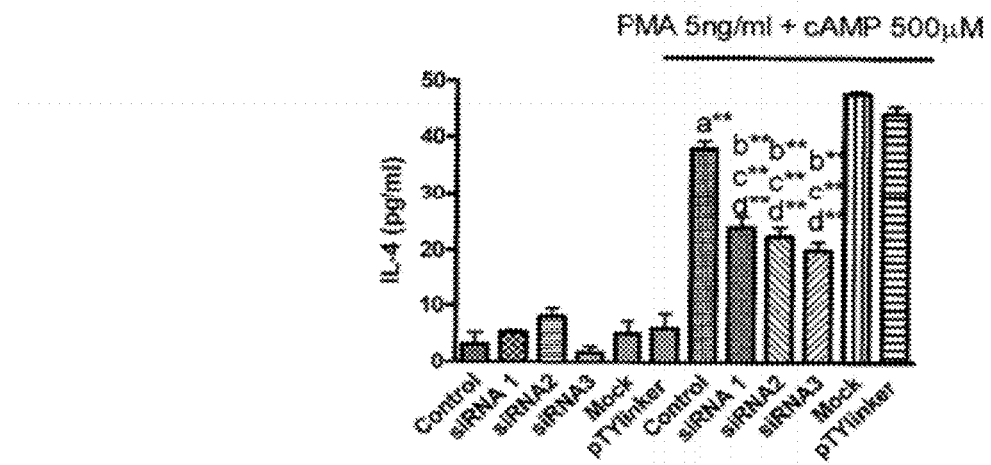
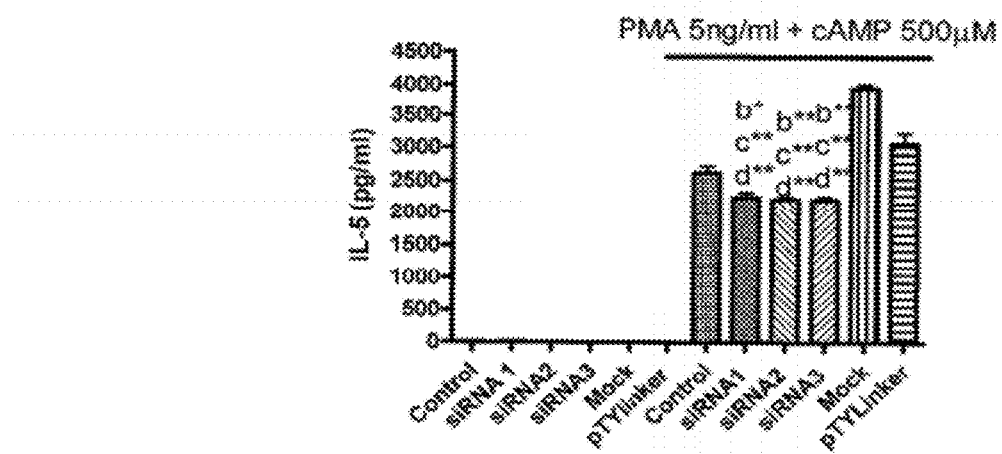

FIG 4
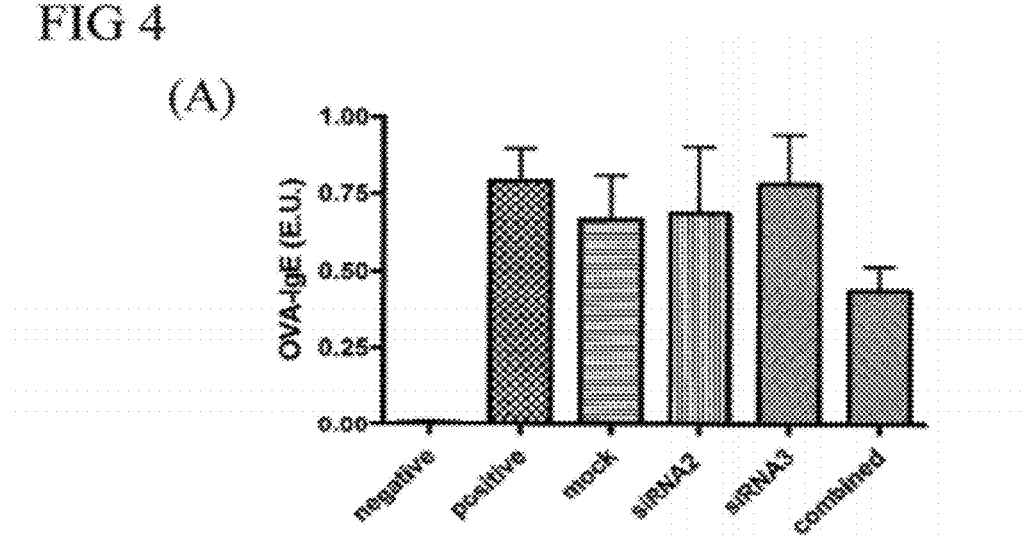
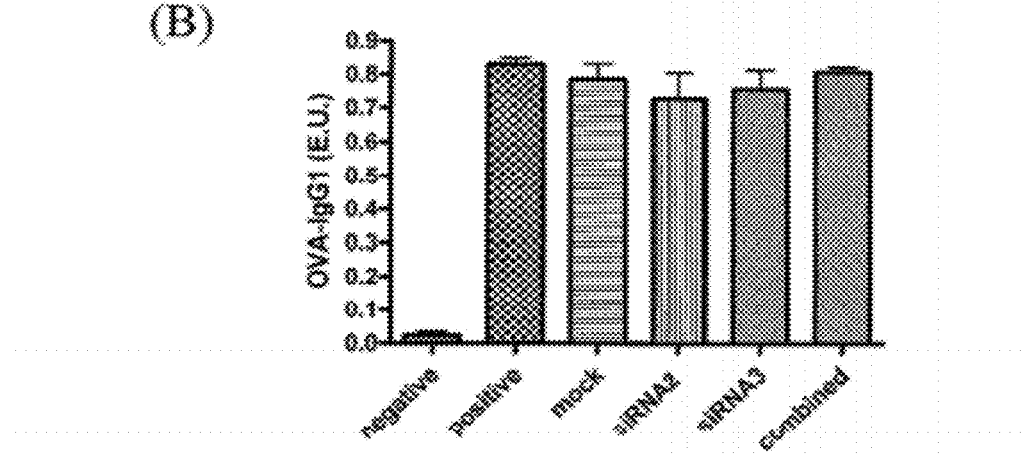
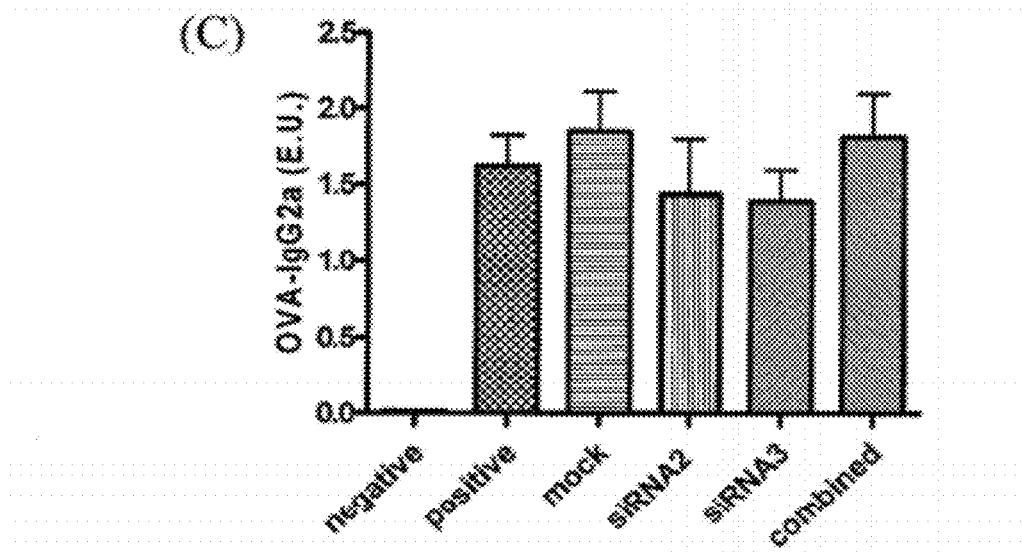

FIG 9
(A)
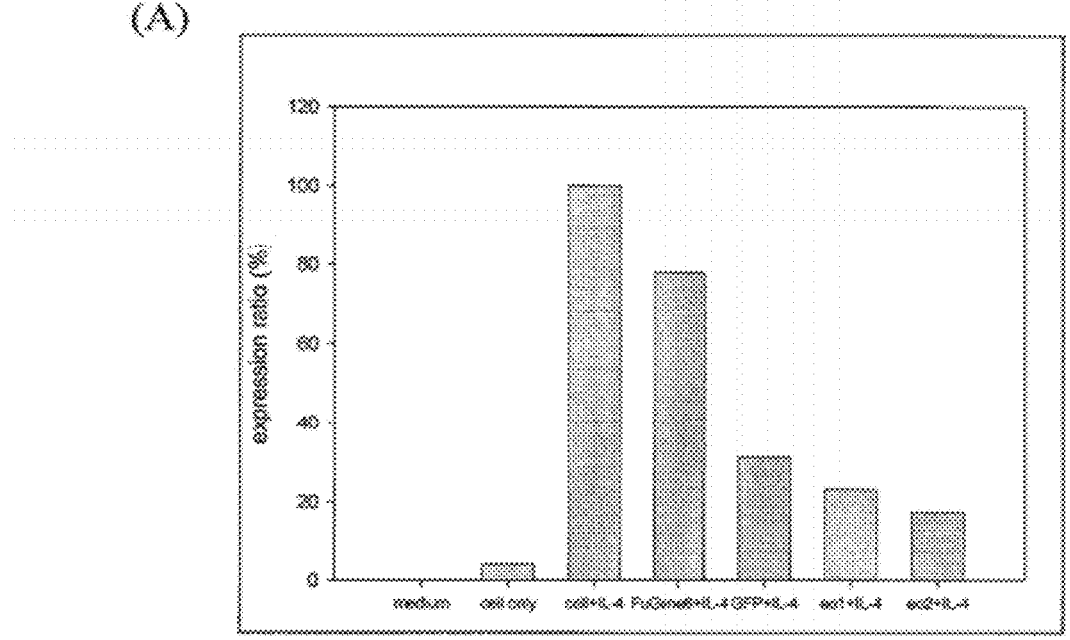
(B)
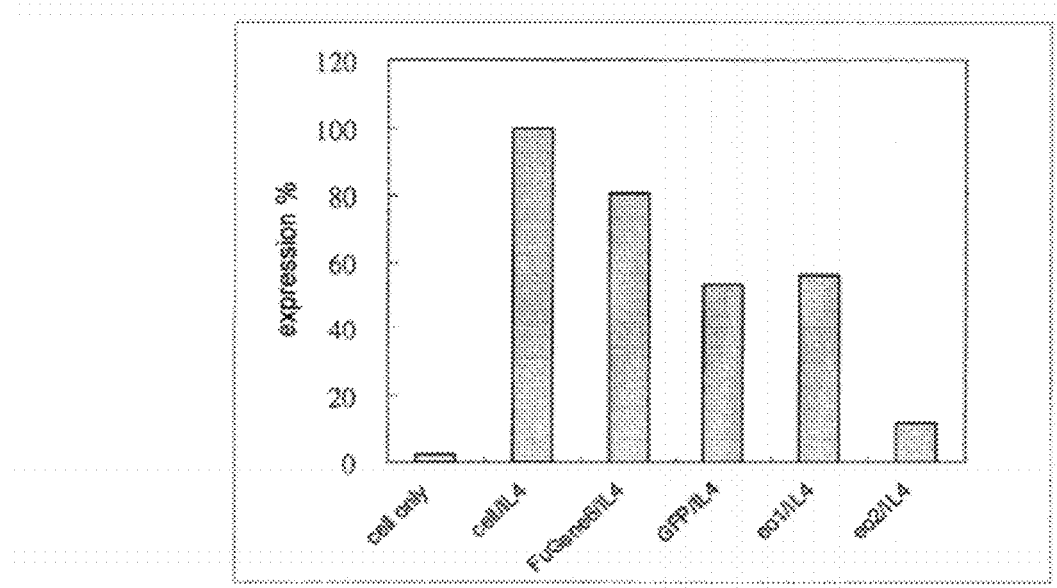

FIG 11
(A)
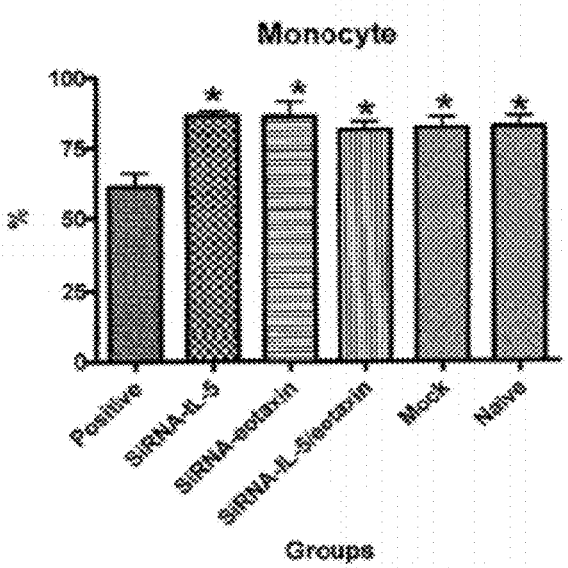
(B)
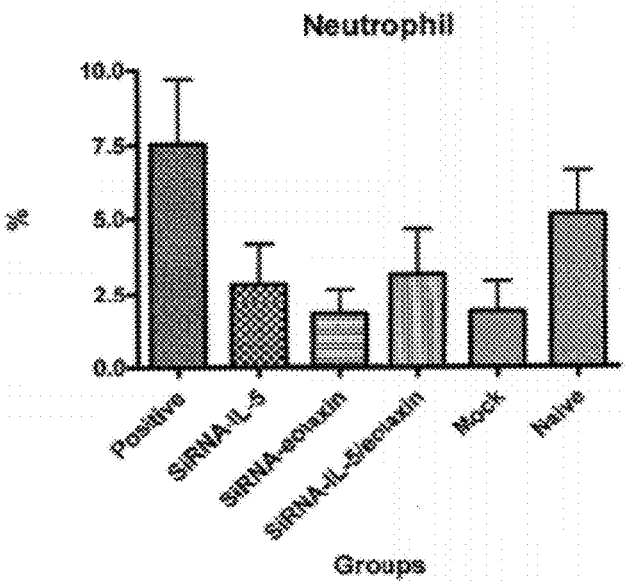

FIG 11
(C)
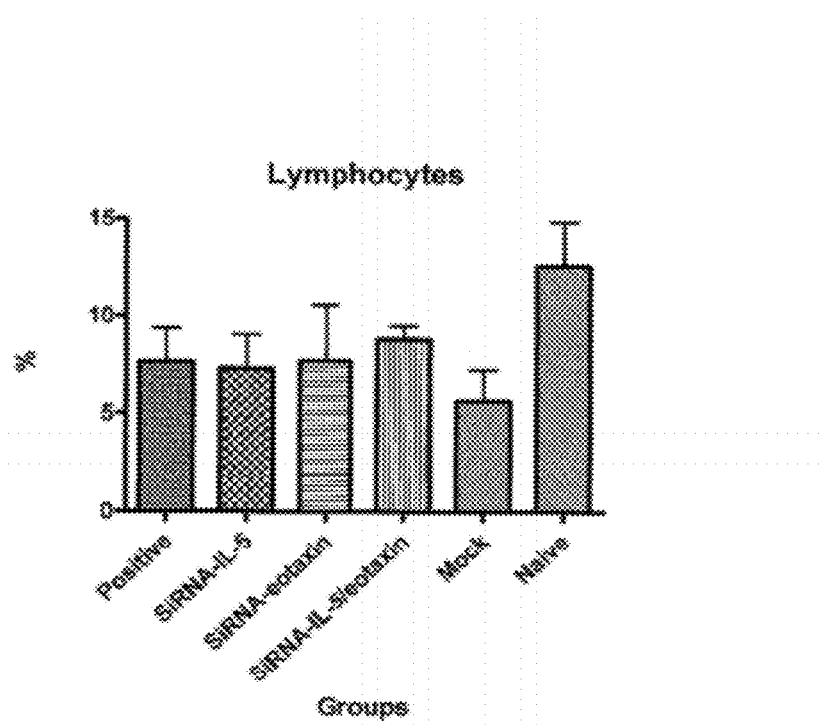
(D)
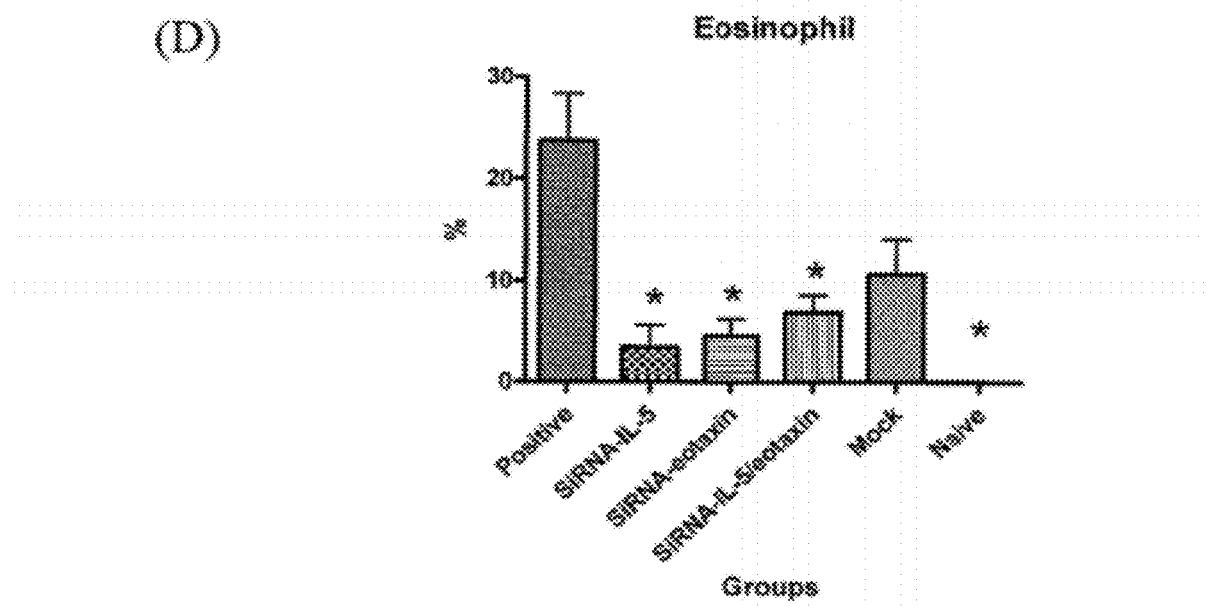

FIG 12
(A)
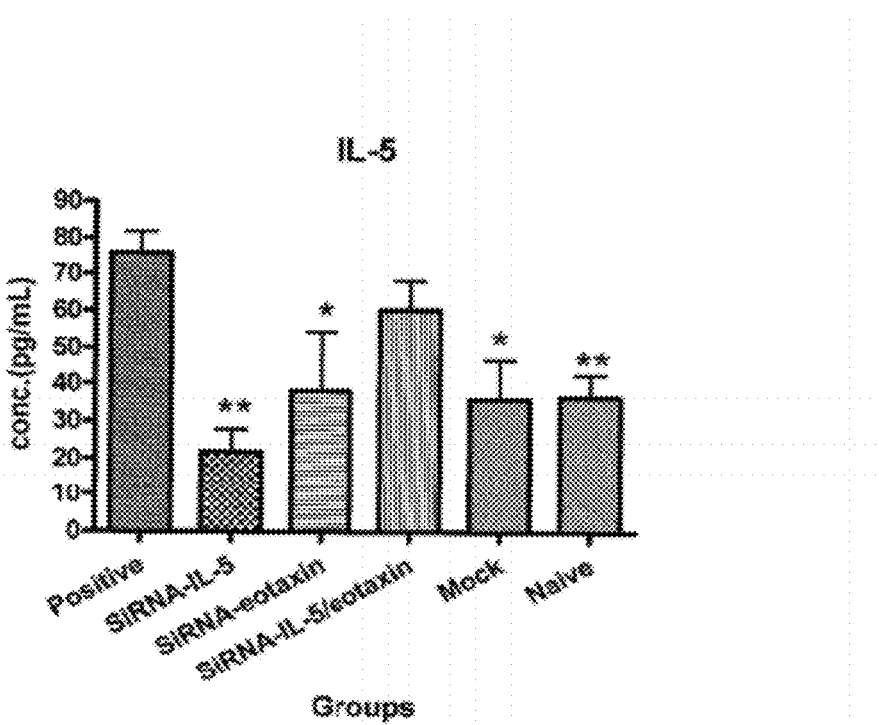
(B)
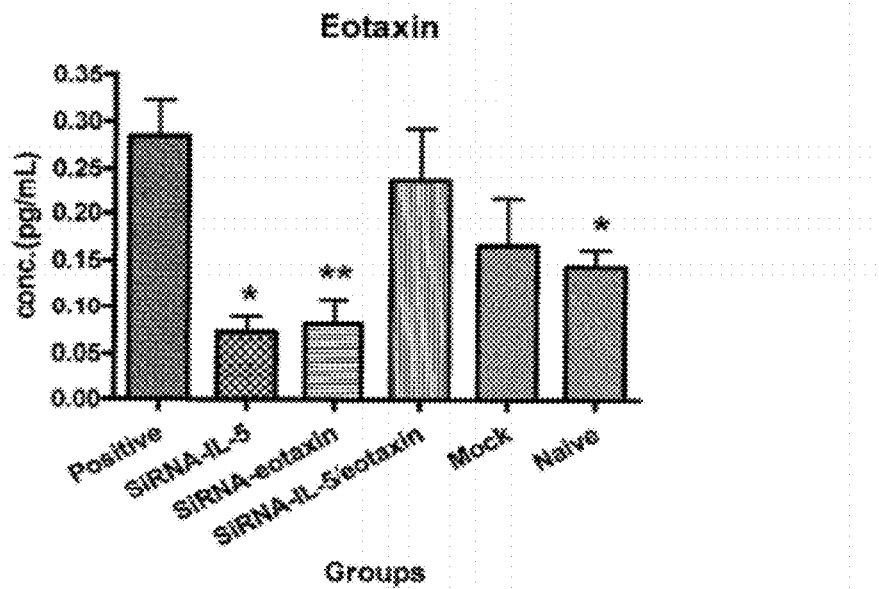

(A)

FIG 13
(B)
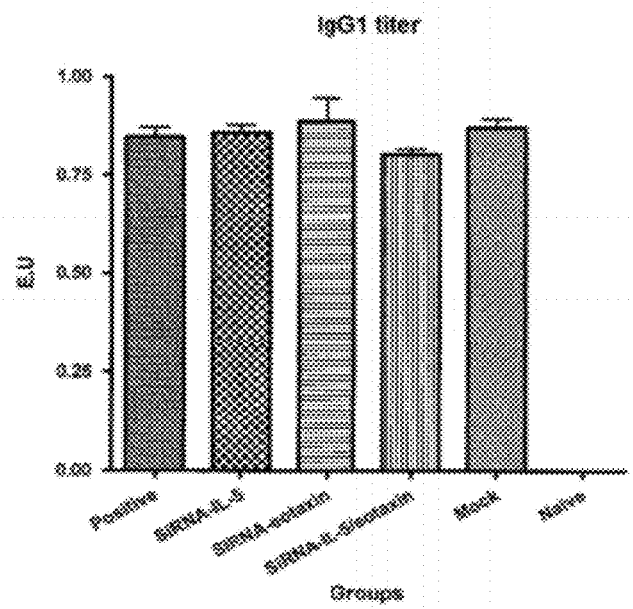
(C)
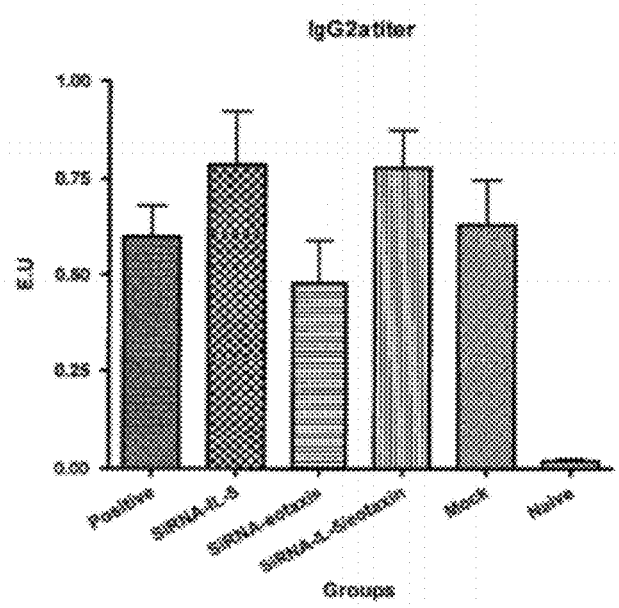

FIG 17
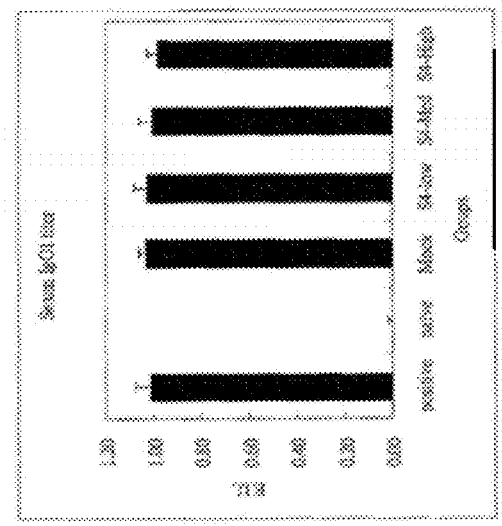
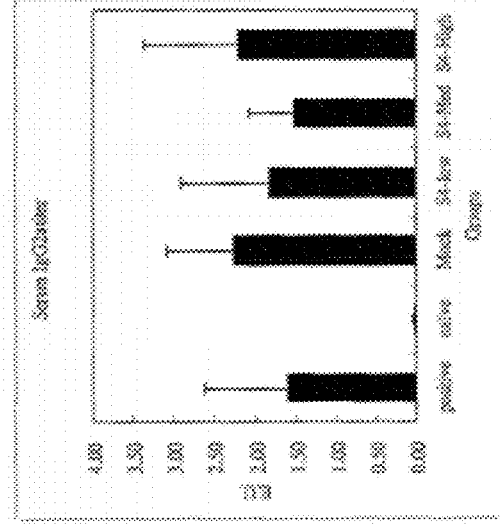
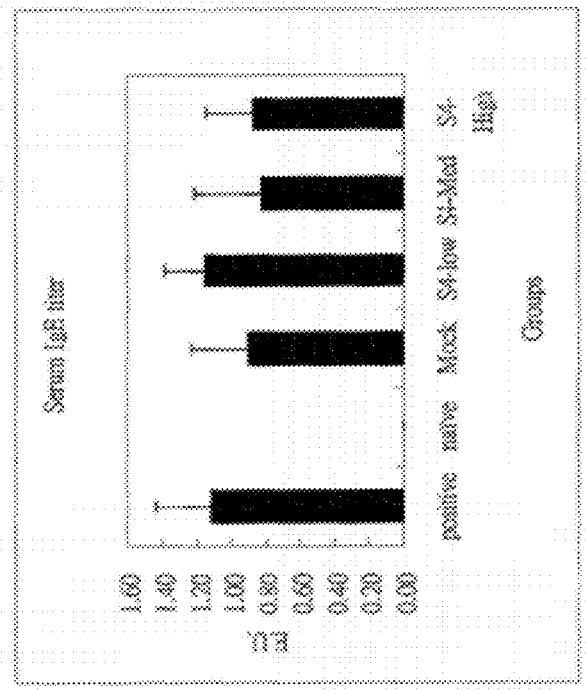

```
                              SEQUENCE LISTING

<160> NUMBER OF SEQ ID NOS: 64

<210> SEQ ID NO 1
<211> LENGTH: 21
<212> TYPE: DNA
<213> ORGANISM: Mus sp.

<400> SEQUENCE: 1
gaagctcagt atccgctgac g                                                 21

<210> SEQ ID NO 2
<211> LENGTH: 21
<212> TYPE: DNA
<213> ORGANISM: Mus sp.

<400> SEQUENCE: 2
ccactgaatc cggatcccat t                                                 21

<210> SEQ ID NO 3
<211> LENGTH: 19
<212> TYPE: DNA
<213> ORGANISM: Mus sp.

<400> SEQUENCE: 3
gatgtctagc aaatcgaaa                                                    19

<210> SEQ ID NO 4
<211> LENGTH: 21
<212> TYPE: DNA
<213> ORGANISM: Mus sp.

<400> SEQUENCE: 4
aagaatcaaa ctgtccgtgg g                                                 21

<210> SEQ ID NO 5
<211> LENGTH: 21
<212> TYPE: DNA
<213> ORGANISM: Mus sp.

<400> SEQUENCE: 5
aagaaattcc tgtagcgcag g                                                 21

<210> SEQ ID NO 6
<211> LENGTH: 21
<212> TYPE: DNA
<213> ORGANISM: Mus sp.

<400> SEQUENCE: 6
```

-continued

```
aatcagactg tgccatgact g                                        21

<210> SEQ ID NO 7
<211> LENGTH: 19
<212> TYPE: DNA
<213> ORGANISM: Mus sp.

<400> SEQUENCE: 7
cttcctgctg ctttatcat                                           19

<210> SEQ ID NO 8
<211> LENGTH: 19
<212> TYPE: DNA
<213> ORGANISM: Mus sp.

<400> SEQUENCE: 8
gtgggtccag gatgccaca                                           19

<210> SEQ ID NO 9
<211> LENGTH: 19
<212> TYPE: DNA
<213> ORGANISM: Mus sp.

<400> SEQUENCE: 9
cacaatggga cgagttagg                                           19

<210> SEQ ID NO 10
<211> LENGTH: 21
<212> TYPE: DNA
<213> ORGANISM: Mus sp.

<400> SEQUENCE: 10
aagctgcacc atgaatgagt c                                        21

<210> SEQ ID NO 11
<211> LENGTH: 21
<212> TYPE: DNA
<213> ORGANISM: Mus sp.

<400> SEQUENCE: 11
aacaccacag agagtgagct c                                        21

<210> SEQ ID NO 12
<211> LENGTH: 21
<212> TYPE: DNA
<213> ORGANISM: Mus sp.

<400> SEQUENCE: 12
aatgtaccag gagccatatc c                                        21

<210> SEQ ID NO 13
<211> LENGTH: 21
<212> TYPE: DNA
<213> ORGANISM: Mus sp.

<400> SEQUENCE: 13
aatgccatct acaggaccca g                                        21

<210> SEQ ID NO 14
<211> LENGTH: 21
<212> TYPE: DNA
<213> ORGANISM: Mus sp.

<400> SEQUENCE: 14
```

```
aacggcagca tggtatggag t                                        21

<210> SEQ ID NO 15
<211> LENGTH: 21
<212> TYPE: DNA
<213> ORGANISM: Mus sp.

<400> SEQUENCE: 15
aaggagctta ttgaggagct g                                        21

<210> SEQ ID NO 16
<211> LENGTH: 21
<212> TYPE: RNA
<213> ORGANISM: Mus sp.

<400> SEQUENCE: 16
gaagcucagu auccgcugac g                                        21

<210> SEQ ID NO 17
<211> LENGTH: 21
<212> TYPE: RNA
<213> ORGANISM: Mus sp.

<400> SEQUENCE: 17
ccacugaauc cggaucccau u                                        21

<210> SEQ ID NO 18
<211> LENGTH: 19
<212> TYPE: RNA
<213> ORGANISM: Mus sp.

<400> SEQUENCE: 18
gaugucuagc aaaucgaaa                                           19

<210> SEQ ID NO 19
<211> LENGTH: 21
<212> TYPE: RNA
<213> ORGANISM: Mus sp.

<400> SEQUENCE: 19
aagaaucaaa cguccgugg g                                         21

<210> SEQ ID NO 20
<211> LENGTH: 21
<212> TYPE: RNA
<213> ORGANISM: Mus sp.

<400> SEQUENCE: 20
aagaaauucc uguagcgcag g                                        21

<210> SEQ ID NO 21
<211> LENGTH: 21
<212> TYPE: RNA
<213> ORGANISM: Mus sp.

<400> SEQUENCE: 21
aaucagacug ugccaugacu g                                        21

<210> SEQ ID NO 22
<211> LENGTH: 19
<212> TYPE: RNA
<213> ORGANISM: Mus sp.

<400> SEQUENCE: 22
```

-continued cuuccugcug cuuuaucau							19

<210> SEQ ID NO 23
<211> LENGTH: 19
<212> TYPE: RNA
<213> ORGANISM: Mus sp.

<400> SEQUENCE: 23
gugggnccag gaugccaca							19

<210> SEQ ID NO 24
<211> LENGTH: 19
<212> TYPE: RNA
<213> ORGANISM: Mus sp.

<400> SEQUENCE: 24
cacaauggga cgaguuagg							19

<210> SEQ ID NO 25
<211> LENGTH: 21
<212> TYPE: RNA
<213> ORGANISM: Mus sp.

<400> SEQUENCE: 25
aagcugcacc augaaugagu c							21

<210> SEQ ID NO 26
<211> LENGTH: 21
<212> TYPE: RNA
<213> ORGANISM: Mus sp.

<400> SEQUENCE: 26
aacaccacag agagugagcu c							21

<210> SEQ ID NO 27
<211> LENGTH: 21
<212> TYPE: RNA
<213> ORGANISM: Mus sp.

<400> SEQUENCE: 27
aauguaccag gagccauauc c							21

<210> SEQ ID NO 28
<211> LENGTH: 21
<212> TYPE: RNA
<213> ORGANISM: Mus sp.

<400> SEQUENCE: 28
aaugccaucu acaggaccca g							21

<210> SEQ ID NO 29
<211> LENGTH: 21
<212> TYPE: RNA
<213> ORGANISM: Mus sp.

<400> SEQUENCE: 29
aacggcagca ugguauggag u							21

<210> SEQ ID NO 30
<211> LENGTH: 21
<212> TYPE: RNA
<213> ORGANISM: Mus sp.

<400> SEQUENCE: 30
aaggagcuua uugaggagcu g                                              21

<210> SEQ ID NO 31
<211> LENGTH: 21
<212> TYPE: DNA
<213> ORGANISM: Homo sapiens

<400> SEQUENCE: 31
cgagaaagag tgcctcaagt a                                              21

<210> SEQ ID NO 32
<211> LENGTH: 21
<212> TYPE: DNA
<213> ORGANISM: Homo sapiens

<400> SEQUENCE: 32
catccagacc agaaaccgaa a                                              21

<210> SEQ ID NO 33
<211> LENGTH: 21
<212> TYPE: DNA
<213> ORGANISM: Homo sapiens

<400> SEQUENCE: 33
cctactacgg aaactcggtc a                                              21

<210> SEQ ID NO 34
<211> LENGTH: 21
<212> TYPE: DNA
<213> ORGANISM: Homo sapiens

<400> SEQUENCE: 34
ggattcctgt tcctgtacat a                                              21

<210> SEQ ID NO 35
<211> LENGTH: 21
<212> TYPE: DNA
<213> ORGANISM: Homo sapiens

<400> SEQUENCE: 35
agaaatacat tgacggccaa a                                              21

<210> SEQ ID NO 36
<211> LENGTH: 21
<212> TYPE: DNA
<213> ORGANISM: Homo sapiens

<400> SEQUENCE: 36
ctggtttgtt gcagccaaag a                                              21

<210> SEQ ID NO 37
<211> LENGTH: 21
<212> TYPE: DNA
<213> ORGANISM: Homo sapiens

<400> SEQUENCE: 37
ttgtaaaggt cctggcaaag a                                              21

<210> SEQ ID NO 38
<211> LENGTH: 21
<212> TYPE: DNA
<213> ORGANISM: Homo sapiens

<400> SEQUENCE: 38

```
ttcagcgact agagagctac a                                          21

<210> SEQ ID NO 39
<211> LENGTH: 21
<212> TYPE: DNA
<213> ORGANISM: Homo sapiens

<400> SEQUENCE: 39
agaccaaact ggccaaggat a                                          21

<210> SEQ ID NO 40
<211> LENGTH: 21
<212> TYPE: DNA
<213> ORGANISM: Homo sapiens

<400> SEQUENCE: 40
aagaacacaa ctgagaagga a                                          21

<210> SEQ ID NO 41
<211> LENGTH: 21
<212> TYPE: DNA
<213> ORGANISM: Homo sapiens

<400> SEQUENCE: 41
aacttcttgg aaaggctaaa g                                          21

<210> SEQ ID NO 42
<211> LENGTH: 21
<212> TYPE: DNA
<213> ORGANISM: Homo sapiens

<400> SEQUENCE: 42
caccttacag gagatcatca a                                          21

<210> SEQ ID NO 43
<211> LENGTH: 21
<212> TYPE: DNA
<213> ORGANISM: Homo sapiens

<400> SEQUENCE: 43
aggacctgct cttacattta a                                          21

<210> SEQ ID NO 44
<211> LENGTH: 21
<212> TYPE: DNA
<213> ORGANISM: Homo sapiens

<400> SEQUENCE: 44
tcattgagga gctggtcaac a                                          21

<210> SEQ ID NO 45
<211> LENGTH: 21
<212> TYPE: DNA
<213> ORGANISM: Homo sapiens

<400> SEQUENCE: 45
agttcaaccg aaacttcgaa a                                          21

<210> SEQ ID NO 46
<211> LENGTH: 21
<212> TYPE: RNA
<213> ORGANISM: Homo sapiens

<400> SEQUENCE: 46
```

```
cgagaaagag ugccucaagu a                                              21

<210> SEQ ID NO 47
<211> LENGTH: 21
<212> TYPE: RNA
<213> ORGANISM: Homo sapiens

<400> SEQUENCE: 47
cauccagacc agaaaccgaa a                                              21

<210> SEQ ID NO 48
<211> LENGTH: 21
<212> TYPE: RNA
<213> ORGANISM: Homo sapiens

<400> SEQUENCE: 48
ccuacuacgg aaacucgguc a                                              21

<210> SEQ ID NO 49
<211> LENGTH: 21
<212> TYPE: RNA
<213> ORGANISM: Homo sapiens

<400> SEQUENCE: 49
ggauuccugu uccuguacau a                                              21

<210> SEQ ID NO 50
<211> LENGTH: 21
<212> TYPE: RNA
<213> ORGANISM: Homo sapiens

<400> SEQUENCE: 50
agaaauacau ugacggccaa a                                              21

<210> SEQ ID NO 51
<211> LENGTH: 21
<212> TYPE: RNA
<213> ORGANISM: Homo sapiens

<400> SEQUENCE: 51
cugguuuguu gcagccaaag a                                              21

<210> SEQ ID NO 52
<211> LENGTH: 21
<212> TYPE: RNA
<213> ORGANISM: Homo sapiens

<400> SEQUENCE: 52
uuguaaaggu ccuggcaaag a                                              21

<210> SEQ ID NO 53
<211> LENGTH: 21
<212> TYPE: RNA
<213> ORGANISM: Homo sapiens

<400> SEQUENCE: 53
uucagcgacu agagagcuac a                                              21

<210> SEQ ID NO 54
<211> LENGTH: 21
<212> TYPE: RNA
<213> ORGANISM: Homo sapiens

<400> SEQUENCE: 54
```
agaccaaacu ggccaaggau a                                      21

<210> SEQ ID NO 55
<211> LENGTH: 21
<212> TYPE: RNA
<213> ORGANISM: Homo sapiens

<400> SEQUENCE: 55
aagaacacaa cugagaagga a                                      21

<210> SEQ ID NO 56
<211> LENGTH: 21
<212> TYPE: RNA
<213> ORGANISM: Homo sapiens

<400> SEQUENCE: 56
aacuucuugg aaaggcuaaa g                                      21

<210> SEQ ID NO 57
<211> LENGTH: 21
<212> TYPE: RNA
<213> ORGANISM: Homo sapiens

<400> SEQUENCE: 57
caccuuacag gagaucauca a                                      21

<210> SEQ ID NO 58
<211> LENGTH: 21
<212> TYPE: RNA
<213> ORGANISM: Homo sapiens

<400> SEQUENCE: 58
aggaccugcu cuuacauuua a                                      21

<210> SEQ ID NO 59
<211> LENGTH: 21
<212> TYPE: RNA
<213> ORGANISM: Homo sapiens

<400> SEQUENCE: 59
ucauugagga gcuggucaac a                                      21

<210> SEQ ID NO 60
<211> LENGTH: 21
<212> TYPE: RNA
<213> ORGANISM: Homo sapiens

<400> SEQUENCE: 60
aguucaaccg aaacuucgaa a                                      21

<210> SEQ ID NO 61
<211> LENGTH: 21
<212> TYPE: DNA
<213> ORGANISM: Mus sp.

<400> SEQUENCE: 61
gaaggcatcc agacccgaaa c                                      21

<210> SEQ ID NO 62
<211> LENGTH: 20
<212> TYPE: DNA
<213> ORGANISM: Mus sp.

<400> SEQUENCE: 62

```
acccatggcg gtgaccatgc                                                    20

<210> SEQ ID NO 63
<211> LENGTH: 20
<212> TYPE: DNA
<213> ORGANISM: Mus sp.

<400> SEQUENCE: 63
aaggtgtgat ggtgggaatg                                                    20

<210> SEQ ID NO 64
<211> LENGTH: 20
<212> TYPE: DNA
<213> ORGANISM: Mus sp.

<400> SEQUENCE: 64
atggctacgt acatggctgg                                                    20
```

SHORT INTERFERENCE RIBONUCLEIC ACIDS FOR TREATING ALLERGIC DISEASES

CROSS-REFERENCE TO RELATED APPLICATION

This application is a co-pending application which claims priority to PCT Application No. PCT/AU2007/000638, filed May 11, 2007, which claims priority to Australian patent application number 2006902491, filed May 11, 2006, both of which are herein incorporated by reference in their entireties.

FIELD OF THE INVENTION

The present invention relates to treatments of allergic diseases. More particularly, the present invention provides compounds, methods and compositions for treating allergic diseases by suppressing the expression of airway-inflammation related genes through RNA mediated interferences.

BACKGROUND OF THE INVENTION

Increasing prevalence of allergic diseases has been noted in most developed and developing countries. Allergic diseases are defined as functional disturbances caused by type I hypersensitivity, i.e., type I immune response mediated by IgE antibodies. The symptoms include pollinosis, bronchial asthma, allergic rhinitis, sinusitis, respiratory distress syndrome, atopic dermatitis and anaphylactic shock. Today, allergic diseases tend to be more severe in civilized societies and have cost a lot of money. Among the people who are suffering from various allergic symptoms, allergic rhinitis is the most common form of allergy. Also, the attack of allergen can sometimes be fatal. According to a statistic data of 1994 conducted by the Pediatrics Department of the Medical College of National Taiwan University, the prevalence rate of allergic rhinitis among students in Taipei city (Taiwan) is over 33%, about 3 times higher than that of asthma (10~11%). The number of patient is also increasing every year. In particular, patients of young children are on rapid rise. Thus, many researchers are devoting themselves in developing an improved solution to reduce economic and physical burden of the patient from such allergic diseases.

In recent years, with the emerging use of post-transcriptional gene silencing technology, in particular, RNA interference (RNAi), as a tool to knock out expression of specific genes in a variety of organisms (Mello and Conte, "Revealing the world of RNA interference", (2004) Nature 431, 338-342; and Scherer and Rossi, "Approaches for the sequence-specific knockdown of mRNA", (2003) Nature Biotechnology, 21, 1457-1465), it is now possible to map protein interactions in cell signaling pathway by systematically silencing functional genes, and thereby providing a new way of developing therapeutics for countless diseases. The present inventors have made extensive clinical researches and experiments and have identified non-coding, short RNA molecules that are capable of suppressing airway inflammation related-gene expression in vitro or in vivo via RNA interference, thus, these identified short RNA molecules are useful as a medicament for treating allergy to alleviate or minimize airway inflammation of a subject.

SUMMARY

The object of this invention is to provide compounds, compositions and methods for suppressing airway inflammation related-gene expression by using short interfering RNA (siRNA) molecules. In particular, this invention features small ribonucleic acid molecules, such as short interfering double-stranded or single-stranded RNA molecules; and methods for suppressing the expression of airway inflammation related-genes using these siRNA molecules.

Thus, in one aspect, this invention features one or more siRNA molecules and methods that independently or in combination suppress the airway inflammation related-gene expression via RNA interference, such as the expression of gata-3, IL-4, IL-5, IL-13 or eotaxin gene encoding proteins that are associated with airway inflammation.

In one embodiment, the invention features an isolated double stranded siRNA molecule that down-regulates expression of airway inflammation related-gene such as gata-3, IL-4, IL-5, IL-13 or eotaxin gene, wherein said siRNA molecule comprises about 19 to 21 base pairs.

In one embodiment, the invention provides an isolated double stranded siRNA molecule that directs cleavage of gata-3, IL-4, IL-5, IL-13 or eotaxin RNA via RNA interference (RNAi), wherein (a) each strand of said siRNA molecule is about 19 to 21 nucleotides in length; and (b) one strand of said siRNA molecule comprises ribonucleotide sequence complementary to said gata-3, IL-4, IL-5, IL-13 or eotaxin RNA to direct cleavage of the gata-3, IL-4, IL-5, IL-13 or eotaxin RNA via RNA interference. In one embodiment, the isolated siRNA molecule of this invention is of murine origin, which comprises a ribonucleotide sequence complementary to a RNA sequence encoded by a nucleic acid sequence chosen from any of SEQ ID NOs. 1 to 15, in which SEQ ID NOs. 1 to 3 represent nucleotide sequences of gata-3 gene at positions 316-336, 1733-1753 and 1306-1324, respectively; and SEQ ID NOs. 4 to 6 represent nucleotide sequences of IL-5 gene at positions 263-283, 636-656 and 1166-1186, respectively; SEQ ID NOs. 7 to 9 represent nucleotide sequences of eotaxin gene at positions 134-152, 282-294 and 583-594, respectively; SEQ ID NOs. 10 to 12 represent nucleotide sequences of IL-4 gene at positions 47-67, 181-201 and 336-356, respectively; and SEQ ID NOs. 13 to 15 represent nucleotide sequences of IL-13 gene at positions 100-120, 154-174 and 238-258, respectively. In another embodiment, the isolated siRNA molecule of this invention is of human origin, which comprises a ribonucleotide sequence complementary to a RNA sequence encoded by a nucleic acid sequence chosen from any of SEQ ID NOs. 31 to 45, in which SEQ ID NOs. 31 to 33 represent nucleotide sequences of gata-3 gene at positions 537-557, 1080-1100 and 185-205, respectively; and SEQ ID NOs. 34 to 36 represent nucleotide sequences of IL-5 gene at positions 196-216, 328-348 and 457-477, respectively; SEQ ID NOs. 37 to 39 represent nucleotide sequences of eotaxin gene at positions 749-769, 269-289 and 335-355, respectively; SEQ ID NOs. 40 to 42 represent nucleotide sequences of IL-4 gene at positions 133-153, 355-375 and 87-107, respectively; and SEQ ID NOs. 43 to 45 represent nucleotide sequences of IL-13 gene at positions 389-409, 137-157 and 431-451, respectively.

In one embodiment, the invention features an isolated siRNA molecule having RNAi activity against a gata-3, IL-4, IL-5, IL-13 or eotaxin RNA. The siRNA molecule is capable of mediating RNA interference (RNAi) that results in cleavage of the gata-3, IL-4, IL-5, IL-13 or eotaxin RNA in vitro or in vivo. In one embodiment, an isolated siRNA molecule of this invention is of murine origin, which comprises a sequence complementary to a target gene RNA, and the nucleic acid sequence of said target gene is any of SEQ ID NOs. 1 to 15. In another embodiment, an isolated siRNA molecule of this invention is of human origin, which comprises a sequence complementary to a target gene RNA, and the nucleic acid sequence of said target gene is any of SEQ ID NOs. 31 to 45. The sequences shown in SEQ ID NOs: 1-15 or 31-45 are not limiting. An isolated siRNA molecule of the invention may comprise any sequence complementary to contiguous gata-3, IL-4, IL-5, IL-13 or eotaxin gene sequence, such as a sequence complementary to about 19 to 21 or more contiguous gata-3, IL-4, IL-5, IL-13 or eotaxin nucleotides. The preferred murine siRNA molecule of this invention comprises a sequence that is at least 80% identical to any of siRNA1 to siRNA15 prepared in accordance with methods described in Examples 1 to 6, and is respectively encoded by a target nucleic acid sequence chosen from SEQ ID NOs 1 to 15. The preferred human siRNA molecule of this invention comprises a sequence that is at least 80% identical to any of siRNA16 to siRNA30 prepared in accordance with methods described in Example 7, and is respectively encoded by a target nucleic acid sequence chosen from SEQ ID NOs 31 to 45.

In one embodiment, the siRNA molecule of this invention may be a single stranded siRNA that mediates RNAi activity in vitro or in vivo, comprising a single stranded polyribonucleotide complementary to a target gene RNA sequence. The target gene may be an airway inflammation-related gene, such as gata-3, IL-4, IL-5, IL-13 or eotaxin gene.

In another aspect, the invention provides a pharmaceutical composition for treating allergy such as pollinosis, bronchial asthma, sinusitis, respiratory distress syndrome, or allergic rhinitis by suppressing airway inflammation related-gene expression, such as the expression of gata-3, IL-4, IL-5, IL-13 or eotaxin gene, using short interfering nucleic acid molecules.

In one embodiment, the invention features a pharmaceutical composition comprising a siRNA molecule of the invention in a pharmaceutically acceptable carrier.

In one embodiment, this invention provides an expression vector of at least one siRNA molecule of this invention, which contains a portion of a target gene of interest, in a manner that allows expression of the siRNA molecules to suppress or counteract the expression of the target gene in vitro or in vivo via RNA interference (RNAi). The target gene may be an airway inflammation-related gene such as gata-3, IL-4, IL-5, IL-13 or eotaxin gene.

In one embodiment, this invention features a method for treating a subject suffering from allergy such as pollinosis, bronchial asthma, sinusitis, respiratory distress syndrome, or allergic rhinitis, by introducing into the subject an expression vector of at least one siRNA molecule, which contains a polyribonucleotide sequence complementary to a portion of an airway inflammation-related gene RNA, in a manner that allows expression of the siRNA molecule to suppress the expression of the airway inflammation-related gene via RNA interference (RNAi), and thereby achieving the purpose of reducing and/or minimizing the allergy symptoms of the subject.

These and other aspects and advantages will become apparent when the Description is read in conjunction with the accompanying Examples. It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 1 is the schematic drawings of murine gata-3 siRNAs in pSEC hydro plasmid and a lentivirus-based vector, in which (A) is a schematic diagram of the siRNA expression cassette; (B) is a schematic diagram of the pSEC hydro plasmid, which contains a hydromycin selection site for selecting a stable clone that expressed siRNAs; and (C) is a schematic diagram of the siRNA-expressing lentiviral vector.

FIG. 4 are the bar diagrams showing the level of serum OVA-specific antibodies including (A) IgE, (B) IgG1 and (C) $IgG_{2a}$ in BALB/c mice treated with gata-3 siRNAs in accordance with one embodiment of this invention.

FIG. 9 illustrates the expressed level of eotaxin in either (A) the culture medium or (B) the cells transfected with the synthesized eotaxin siNAs including siRNA7, siRNA8 and siRNA9 in accordance with one preferred embodiment of this invention.

FIG. 11 illustrates the cell profiles including (A) monocytes, (B) neutrophils, (C) lymphocytes, and (D) eosinophils in BALF collected from the mice in accordance with one embodiment of this invention. Total cell counts were determined on 1 ml HBSS, and data were expressed as mean±SEM, * p<0.01, as compared with the saline group.

FIG. 12 illustrates the level of (A) IL-5 and (B) eotaxin in BAL fluid of mice of Example 4 as measured by ELISA.

FIG. 17 are the bar diagrams showing the level of serum OVA-specific antibodies including (A) IgE, (B) IgG1 and (C) $IgG_{2a}$ in BALB/c mice of Example 5, which were treated with high, medium or low dosage of siRNA5, respectively.

DESCRIPTION OF THE INVENTION

Figure 2:
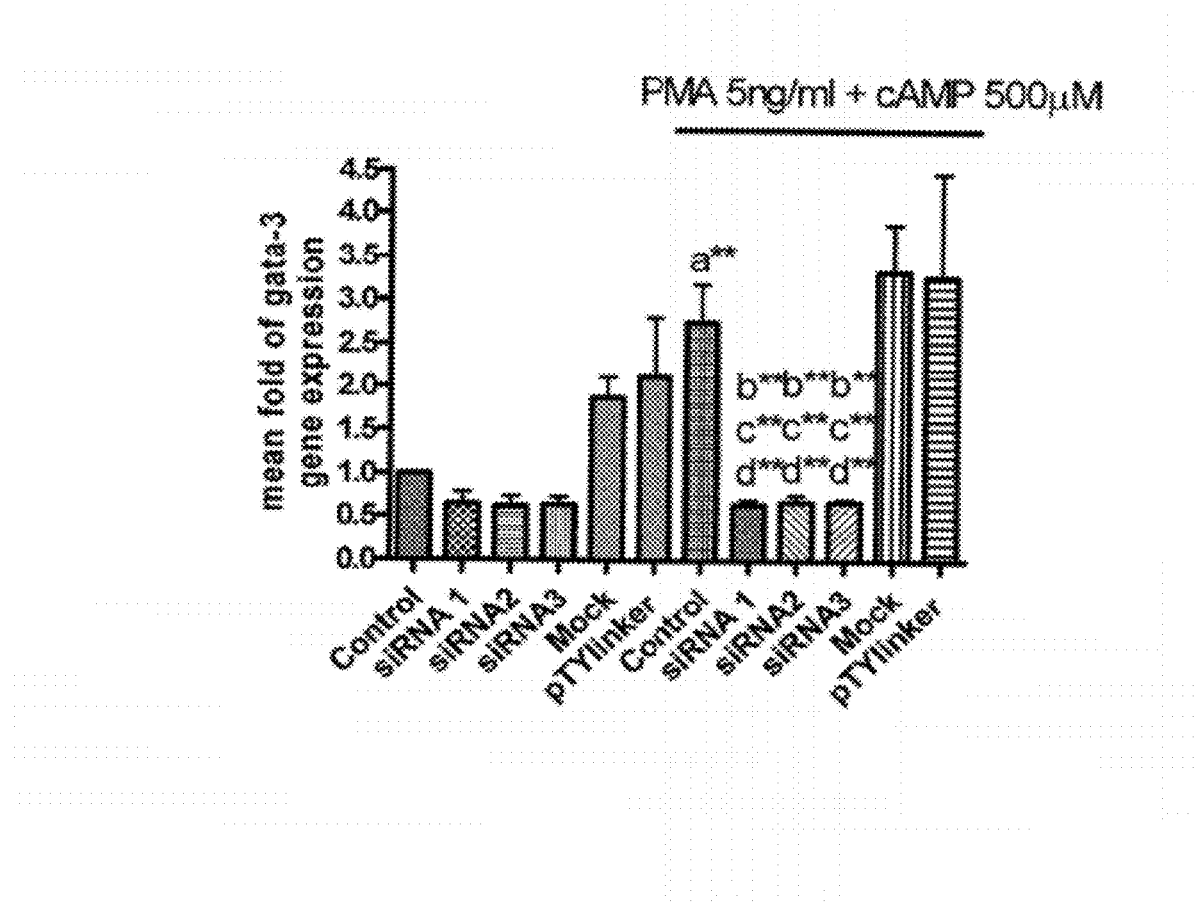
FIG. 2 illustrates the reduction of gata-3 gene expression and Th2 cytokines release after the transduction of gata-3 siRNAs in EL-4 cells that were treated with a combination of PMA (5 ng/ml) and cAMP (500 mM) for 24 hrs, detection of the expressed gata-3 gene and proteins was confirmed by (A) real time PCR and (B) western blotting, respectively; and (C) Th2 cytokines release was detected by sandwich-ELISA assay. In the figure, "Mock" refers to mock transduction control contained of siRNA negative control from Ambion; "PTYlinker" refers to empty vector. a $p<0.01$, as compared with no pre-treatment control group; b $p<0.01$, as compared with PMA 5 ng/ml+cAMP 500 mM control group; c $p<0.01$, as compared with PMA 5 ng/ml+cAMP 500 mM Mock group; d $P<0.01$, as compared with PMA 5 ng/ml+cAMP 500 mM PTYlinker group.

The embodiments described and the terminology used herein are for the purpose of describing exemplary embodiments only, and are not intended to be limiting. The scope of the present invention is intended to encompass additional embodiments not specifically described herein, but that would be apparent to one skilled in the art upon reading the present disclosure and practicing the invention.

The present invention is directed to a novel solution for treating allergic diseases such as pollinosis, bronchial asthma, allergic rhinitis, sinusitis, respiratory distress syndrome, atopic dermatitis or anaphylactic shock, by use of short interfering ribonucleic acid (siRNA) molecules. Applicant demonstrates herein that particular isolated short interfering ribonucleic acids with ribonucleotide sequences complementary to at least a portion of a target gene RNA such as an airway inflammation related-gene RNA, are capable of resulting in the cleavage of the expressed target gene RNA via RNA interference mechanism.

RNA interference refers to the process of sequence specific post-transcriptional gene silencing in animals mediated by short interfering RNAs (siRNAs) (Fire et al., "Potent and specific genetic interference by double-stranded RNA in *Caenorhabditis elegans*" (1998) Nature 391, 806-811). The process of post-transcriptional gene silencing is thought to be an evolutionally conserved cellular defense mechanism used to prevent the expression of foreign genes (Andrew Fire, "RNA-triggered gene silencing" (1999), Trends Genet. 15 (9), 358-363). Such protection from foreign gene expression may have evolved in response to the production of double-stranded RNAs (dsRNAs) derived from viral infection or random integration of transposon elements into a host genome via a cellular response that specifically destroys homologous single-stranded RNA or viral genomic RNA. The presence of (dsRNAs in cells triggers the RNAi response through a mechanism that has not yet been fully identified.

The presence of dsRNAs in cells results in the activation of a ribonuclease enzyme referred to as Dicer. Dicer is involved in the processing the dsRNAs into short pieces of dsRNA known as short interfering RNAs (siRNAs) (Berstein et al., "Role for a bidentate ribonuclease in the initiation step of RNA interference" (2001) Nature, 409, 363-366). Short interfering RNAs derived form the action of Dicer is usually about 21 to 23 nucleotides in length and comprises about 19 base pairs duplexes. The RNAi response also features an endonuclease complex containing a siRNA, commonly referred to as an RNA-induced silencing complex (RISC), which mediates cleavage of single-stranded RNA having sequence homology to the siRNA. Cleavage of the target RNA takes place in the middle of the region complementary to the guide sequence of the siRNA duplex. As such, siRNA molecules of this invention can be used to mediate gene silencing via interaction with RNA transcripts or by interaction with particular gene sequences, wherein such interaction results in gene silencing either at the transcriptional level or post-transcriptional level. For a general review on the RNA interference technique, please see Mello and Conte, "Revealing the world of RNA interference", (2004) Nature 431, 338-342; and Scherer and Rossi, "Approaches for the sequence-specific knockdown of mRNA", (2003) Nature Biotechnology, 21, 1457-1465.

Thus, in one embodiment, this invention provides one or more siRNA molecules that independently or in combination suppress the airway inflammation related-gene expression of a subject via RNA interference, so that expression of the airway inflammation related-gene such as gata-3, IL-4, IL-5, IL-13 or eotaxin gene are suppressed or delayed, thereby minimizing and/or alleviating the inflammation responses of the subject.

In one embodiment, the invention provides an isolated double stranded siRNA molecule that directs cleavage of gata-3, IL-4, IL-5, IL-13 or eotaxin RNA via RNA interference (RNAi), wherein (a) each strand of said siRNA molecule is about 19 to 21 nucleotides in length; and (b) one strand of said siRNA molecule comprises ribonucleotide sequence complementary to said gata-3, IL-4, IL-5, IL-13 or eotaxin RNA to direct cleavage of the gata-3, IL-4, IL-5, IL-13 or eotaxin RNA via RNA interference.

The isolated siRNA molecule of this invention may be of murine or human origin. Specifically, the isolated murine siRNA molecule of this invention targets a ribonucleotide sequence encoded by a nucleic acid chosen from SEQ ID NOs. 1 to 15, in which SEQ ID NOs. 1 to 3 represent nucleotide sequences of gata-3 gene at positions 316-336, 1733-1753 and 1306-1324, respectively; and SEQ ID NOs. 4 to 6 represent nucleotide sequences of IL-5 gene at positions 263-283, 636-656 and 1166-1186, respectively; SEQ ID NOs. 7 to 9 represent nucleotide sequences of eotaxin gene at positions 134-152, 282-294 and 583-594, respectively; SEQ ID NOs. 10 to 12 represent nucleotide sequences of IL-4 gene at positions 47-67, 181-201 and 336-356, respectively; and SEQ ID NOs. 13 to 15 represent nucleotide sequences of IL-13 gene at positions 100-120, 154-174 and 238-258, respectively. The isolated human siRNA molecule of this invention targets a ribonucleotide sequence encoded by a nucleic acid chosen from SEQ ID NOs. 31 to 45, in which SEQ ID NOs. 31 to 33 represent nucleotide sequences of gata-3 gene at positions 537-557, 1080-1100 and 185-205, respectively; and SEQ ID NOs. 34 to 36 represent nucleotide sequences of IL-5 gene at positions 196-216, 328-348 and 457-477, respectively; SEQ ID NOs. 37 to 39 represent nucleotide sequences of eotaxin gene at positions 749-769, 269-289 and 335-355, respectively; SEQ ID NOs. 40 to 42 represent nucleotide sequences of IL-4 gene at positions 133-153, 355-375 and 87-107, respectively; and SEQ ID NOs. 43 to 45 represent nucleotide sequences of IL-13 gene at positions 389-409, 137-157 and 431-451, respectively.

A preferred murine siRNA molecule of this invention comprises a sequence that is complementary to a target gene RNA, or is at least 80% identical to any of siRNA1 to siRNA15 (represented by SEQ ID NOs 16 to 30 respectively) prepared in accordance with the methods described in Examples 1 to 6, said siRNAs are encoded by any nucleic acid sequences chosen form SEQ ID NOs. 1 to 15. The exact murine nucleic acid sequences for SEQ ID NOs. 1 to 15, and ribonucleic acid sequences for SEQ ID NOs. 16 to 30 are listed in Table 1. A preferred human siRNA molecule of this invention comprises a sequence that is complementary to a target gene RNA, or is at least 80% identical to any of siRNA16 to siRNA30 (represented by SEQ ID NOs 46 to 60, respectively) prepared in accordance with the methods described in Example 7, said human siRNAs are encoded by any nucleic acid sequences chosen form SEQ ID NOs 31 to 45. The exact human nucleic acid sequences for SEQ ID NOs. 31 to 45, and ribonucleic acid sequences for SEQ ID NOs. 46 to 60 are listed in Table 2.

The siRNA molecule of this invention may be a single stranded siRNA that mediates RNAi activity in vitro or in vivo, comprising a single stranded polyribonucleotide having complementarity to a target gene RNA sequence. Preferably, the siRNA is at least 80% identical to the siRNAs directed to the target gene RNAi, said target gene comprises a nucleic acid sequence chosen form any of SEQ ID NOs. 1 to 15 or 31 to 45. The target gene may be an airway inflammation-related gene such as gata-3, IL-4, IL-5, IL-13 or eotaxin gene.

Currently, there are 5 different ways for generating siRNAs for gene silencing studies, including chemical synthesis, in vitro transcription, digestion of long dsRNA by an RNase III family enzyme, expression in cells from an siRNA expression plasmid or viral vector, and expression in cells from a real time polymerase chain reaction (RT-PCR)-derived siRNA expression cassette. The first three methods involve in vitro preparation of siRNAs that are then introduced directly into cells by lipofection, electroporation or other technique. The last two methods rely on the introduction of DNA-based vectors and cassettes that express siRNA within the cells.

The siRNA molecules of this invention were cloned by RT-PCR expression cassette as described in the Examples of this invention using selected target gene sequence as a template. Alternatively, they may be obtained by the above-identified in vitro preparation and/or chemical synthesis by protocols known in the art. The siRNA molecules are then put into an appropriate vector and deliver into a cell for expression. Once expressed, the siRNA molecules interact with the target mRNA and generate an interference RNA response.

The siRNA molecule of this invention can be used alone, or in combination with other therapies, to prevent or treat allergic diseases such as pollinosis, bronchial asthma, allergic rhinitis, sinusitis, respiratory distress syndrome, atopic dermatitis or anaphylactic shock. The siRNA molecules may comprise a delivery vehicle such as liposomes for administration to a subject, carriers, and diluents and/or can be present in pharmaceutically acceptable formulations. Methods for delivering nucleic acid molecules are well known in this art, including, but are not limited to, encapsulation in liposomes, iontophoresis, or by incorporation into other vesicles, such as biodegradable polymers, hydrogel, cyclodextrins, or by proteinaceous vectors. For a more general approach of delivering nucleic acid molecules, one may refer to, for example, U.S. Pat. No. 6,395,713, its entire content is incorporated herein by reference.

Thus, this invention features a pharmaceutical composition comprising one or more siRNA in an acceptable carrier. The siRNAs of this invention can be administered and introduced into a subject by any standard means. When it is desired to use a liposome delivery mechanism, as exemplified in the Examples of this invention, Lipofectamine liposome formulation is preferred and administered in a standard protocol.

The ribonucleic acid molecules of this invention and compositions may be administered orally, topically, parenterally, by inhalation or spray in dosage unit formulation containing conventional non-toxic pharmaceutically acceptable carriers, adjuvants and/or vehicles. The term "parenterally" as used herein includes percutaneous, subcutaneous, intravascular, intramuscular or intrathecal injection or infusion techniques and the like. Compositions intended for oral, topical, parenteral and/or inhalation use can be prepared according to any method known to the art. Preferably, the siRNA molecules of this invention is formulated into an aerosol or spray formulation for use in an inhalation device such as a nebulizer, a metered dose inhaler, or an insufflator, providing rapid local uptake of the nucleic acid molecules into airway tissues.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the present invention, the preferred methods and materials are now described. All publications mentioned are incorporated herein by reference. Unless mentioned otherwise, the techniques employed or contemplated herein are standard methodologies well known to one of ordinary skill in the art. The materials, methods and examples are illustrative only and not limiting.

The singular forms "a", "and", and "the" are used herein to include plural referents unless the context clearly dictates otherwise. Other than in the operating examples, or where otherwise indicated, all numbers expressing quantities of ingredients, reaction conditions, and so forth used in this application are to be understood as being modified in all instances by the term "about." Accordingly, unless the contrary is indicated, the numerical parameters set forth in this application are approximations that may vary In depending upon the desired properties sought to be obtained by the present invention.

EXAMPLES

The following Examples are provided to illustrate certain aspects of the present invention and to aid those of skilled in the art in practicing this invention. These Examples are in no way to be considered to limit the scope of the invention in any manner.

Statistical Analysis

All values in this study refer to mean±S.E.M. (standard error mean) of at least three separate experiments. Statistically significant differences among groups were analyzed with one-way ANOVA followed by Scheffe for Post Hoc comparison by using SPSS software. The minimal level of significance was a p value of <0.05.

Construction of Murine siRNAs and their Uses in Suppressing Airway Inflammation

Example 1

Production of Murine Gata-3 siRNAs Constructs and the Transfection of EL-4 Cells with the Obtained Gata-3 siRNAs Construction of Murine Gata-3 siRNAs Three murine gata-3 target sequences were selected for preparation of gata-3 siRNAs: siRNA1, using target sequence at position 316-336: GAAGCTCAGTATCCGCTGACG (SEQ ID NO: 1); siRNA2, using target sequence at position 1733-1753: CCACTGAATCCGGATCCCATT (SEQ ID NO: 2); and siRNA3, using target sequence at position 1306-1324: GATGTCTAGCAAATCGAAA (SEQ ID NO: 3). Negative control siRNA (commercial kit provided from Ambion, Austin, Tex. USA) were synthesized by PCR-derived siRNA expression cassettes according to the manufacturer's instructions (Ambion) and were then cloned into pSEC™ hygro plasmid (Ambion). The siRNA expression cassette and the construction of murine gata-3 siRNAs in pSEC™ hygro plasmids were illustrated in FIGS. 1A and 1B, respectively.

Transfecting EL-4 Cells with the Synthetic Murine Gata-3 siRNA Constructs

Mouse lymphoma cell line, EL-4 cells (obtained from American Type Cell Cuture, $4 \times 10^5$ cells/ml) were maintained and cultured on 6-well plates, and were transfected with the plasmids of Example 1 the following day with the aid of the lipofectamine 2000 (Invitrogen, Carisbad, Calif. USA). Specifically, 5 µg pSEC™ hygro plasmid contained murine gata-3 siNAs and 9 µl lipofectamine 2000 were allowed to form complexes in a period of 25 min at room temperature in antibiotic-free DMEM medium. The complexes were then added to EL-4 cells maintained and cultured in 6-well dishes and further incubated for another 24 hrs. For the selection of cells with high expression rate of siRNA, stable clones of murine Gata-3 siRNA expressed cells and negative control siRNA were selected by use of 500 µg/ml hygromycin contained medium, and the selected clones were maintained in 250 µg/ml hygromycin contained medium. The transfection of murine gata-3 siRNAs in EL-4 cells was confirmed by the detection of murine gata-3 gene expression either in RNA level by RT-PCR analysis or in protein level by ELSA assay.

RT-PCR Total RNA of EL-4 cells transfected with murine gata-3 siRNAs was isolated using RNAbee (AMS Biotechnology, Abingdon, UK) according to the manufacturer's instructions. RT-PCR was performed to determine relative quantities for GATA-3 and β-actin. Reverse transcription of RNA is performed in a final volume of 20 µl. Reaction tubes contained 4 µl 5× first strand buffer (50 mM Tris-HCl, 3 mM $MgCl_2$); 1 µl of 10 mM mixed of all 4 deoxynucleotides; 1 µl of 0.1 M dithiothretitol; and 1 µl of Superscript reverse transcriptase. RNA and de-ionized water in a final volume of 12 µl were heated at 70° C. for 10 min, and then chilled on ice. RNA sample were added to the reaction tubes, incubated at 42° C. for 50 min, heated to 70° C. for 10 min to denature the reverse transcriptase and then stored at −20° C. The primer sequences of murine GATA-3 are: sense GAAGGCATCCAGACCCGAAAC (SEQ ID NO: 61), antisense ACCCATGGCGGTGACCATGC (SEQ ID NO: 62); murine β-actin: sense AAGGTGTGATGGTGGGAATG (SEQ ID NO: 63), antisense ATGGCTACGTACATGGCTGG (SEQ ID NO: 64). In PCR reaction mixture, the following components were added: 0.5 µl of 2.5 µM dNTP; 2.5 µl of sense primer and antisense primer; 2.5 µl of 10×PCR buffer, 1 µl cDNA; 0.1 µl of Taq polymerase; and 15.9 µl of de-ionized water. After an initial incubation at 94° C. for 3 min, these primers were amplified in cycles as follows: (1) 94° C. for 30 sec; (2) 56° C. for 45 sec; (3) 72° C. for 40 sec for β-actin; and (1) 94° C. for 1 min; (2) 62° C. for 1 min; (3) 72° C. for 1 min for GATA-3, final 72° C. for 10 min.

After amplification, PCR products were subjected to electrophoresis, which was carried out for 0.5 hr at 100 volts in 2% agarose gel prepared in TBE buffer (80 mM Tri-Borate, 2 mM EDTA, pH 8.0). After electrophoresis, gels were stained with 0.1 µg/ml ethidium bromide and examined under ultraviolet light and photographed.

ELISA Assay EL-4 Cells ($1 \times 10^7$ cells/ml) of Example 1 were washed twice with ice-cold phosphate-buffered saline. Then, 200 µl lysis buffer (50 mM Tris-HCl, 1% NP-40, 150 mM NaCl, 1 mM EGTA, 1 mM phenylmethylsulfonyl fluoride, leupeptin 1 mg/ml, pepstatin 1 mg/ml, $NaVO_4$ 0.5M, pH 7.4) was added to each dish; the lysed cell were scarped from the dishes and then incubated in eppendorfs for 30 min at 4° C. Then, these eppendorfs were centrifuged in a speed of 14,000 rpm at 4° C. for 20 min, and the supernatant from each eppendorf was collected. Aliquots of the collected supernatant were mixed with 4× protein sample buffer (31.25 mM Tris-HCl pH6.8, 1% SDS, 25% β-mercaptoethanol, 0.00625% bromophenol blue, and 50% (v/v) glycerol) and boiled for 5 min. Protein samples were run on 10% SDS-PAGE gels and electrophoresed proteins were transfer onto PVDF membrane. Membranes were then blocked with 5% milk in Tris buffered saline containing 0.1% Tween and incubated with primary antibody. Horseradish peroxidase-labeled secondary antibody was used and the bands were detected with chemiluminescence reagents in accordance with the manufacturer's instructions (PerkinElmer Life Science, Inc. Boston, Mass.), and then exposed to X-ray film.

Example 2

Effects of Murine Gata-3 RNAi on Cytokines Release in EL-4 Cells of Example 1

The level of cytokines secreted by EL-4 cells of Example 1 was measured, so as to further confirm the effect of gata-3 siRNA constructs in inhibiting allergic-related Th2 cytokines gene expression. For this purpose, after 3 days infection, EL-4 cells of Example 1 were stimulated with or without the combined treatment of phorbol-12-myristate 13-acetate (PMA, 5 ng/ml) and cAMP (500 μM) for 24 hrs, then cell medium was collected for a measurement of gata-3 gene expression and GATA-3 protein expression in accordance with the procedures described in Example 1, and cytokines (including IL-4 and IL-5) releases were measured according to procedures described below.

Measurement of Cytokines The level of cytokines were detected by sandwich-ELISA assay. Briefly, anti-cytokine's antibodies (either anti-IL-4 or anti-IL-5 antibodies) diluted with $NaHCO_3$ buffer solution (pH 9.6) were added to a 96-well culture dish and incubated for overnight at 4° C. The following day, the culture dish was rinsed with 3% BSA contained-PBS for 3 times at room temperature in a period of 1 hr. Samples to be tested were then added and reacted at 37° C. for 2 hrs or at 4° C. overnight. After the reaction was completed, biotin-conjugated anti-cytokine's antibodies diluted with 1% BSA contained PBS were then added to the culture dish and incubated at room temperature for an hour, and streptavidin-conjugated peroxidase was added subsequently and reacted for another 1 hr. Finally, 0.2 ml of enzyme substrate solution (4 mg O-phenylenediamine dissolved in 20 ml of 0.1 M phosphate-citrate solution containing 0.001% $H_2O_2$) was added to each well, and let stand in darkness at room temperature for 30 min. Absorbance at 450 nm of each well was detected and read by microplate autoreader. The sensitivity of this sandwich-ELISA assay is 15 μg/ml for IL-4, and 20 μg/ml for IL-5, respectively.

The results were illustrated in FIG. 2. The levels of both gata-3 gene (FIG. 2A) and GATA-3 protein (FIG. 2B) were inhibited significantly in the presence of the combined treatment of PMA and cAMP, as compared with that of the control, indicating that gata-3 RNAi is effective in counteracting both PMA-dependent and cAMP-dependent gene and protein expressions. Furthermore, both the levels of IL-4 and IL-5 released upon stimulation of the combined treatment of PMA and cAMP were also suppressed by gata-3 RNAi through the expression of gata-3 gene (FIG. 2C).

Example 3

Effects of Gata-3 RNai on Murine Model of Asthma 3.1 Cloning of Murine Gata-3 siRNAs into Lentiviral Vectors Murine gata-3 siRNAs including siRNA1, siRNA2 and siRNA3 as described in Example 1.1 were cloned into pGEM-T easy vector (Promega, Madison, Wis.) by TA cloning, and restriction enzyme digested the pGEM-T easy vectors containing siRNAs at EcoRI site. The siRNA fragments with EcoRI size in both ends were cloned into pTY linkers (FIG. 1C). The lentiviral vectors used in this experiment were the third generated self-inactivated vector (SIV) provided by Dr. Li-Hua Hwang (Hepatitis Research Center, National Taiwan University Hospital). The siRNA lentiviral vectors were produced by calcium phosphate-mediated transient transfection of HEK-293T cells. Briefly, HEK-293T cells were co-transfected with appropriate amounts of vector plasmids including helper construct, envelope plasmid, tat plasmid, and lentiviral vector plasmid. The viruses were collected from the culture supernatants on day 2 after transfection and were concentrated by 33-folds through ultra-centrifugation. The concentration of different viral vectors used for transduction on EL-4 were MOI=1.4.

3.2 Application of Gata-3 siRNAs Lentivirus into Murine Model of Asthma

Figure 3:
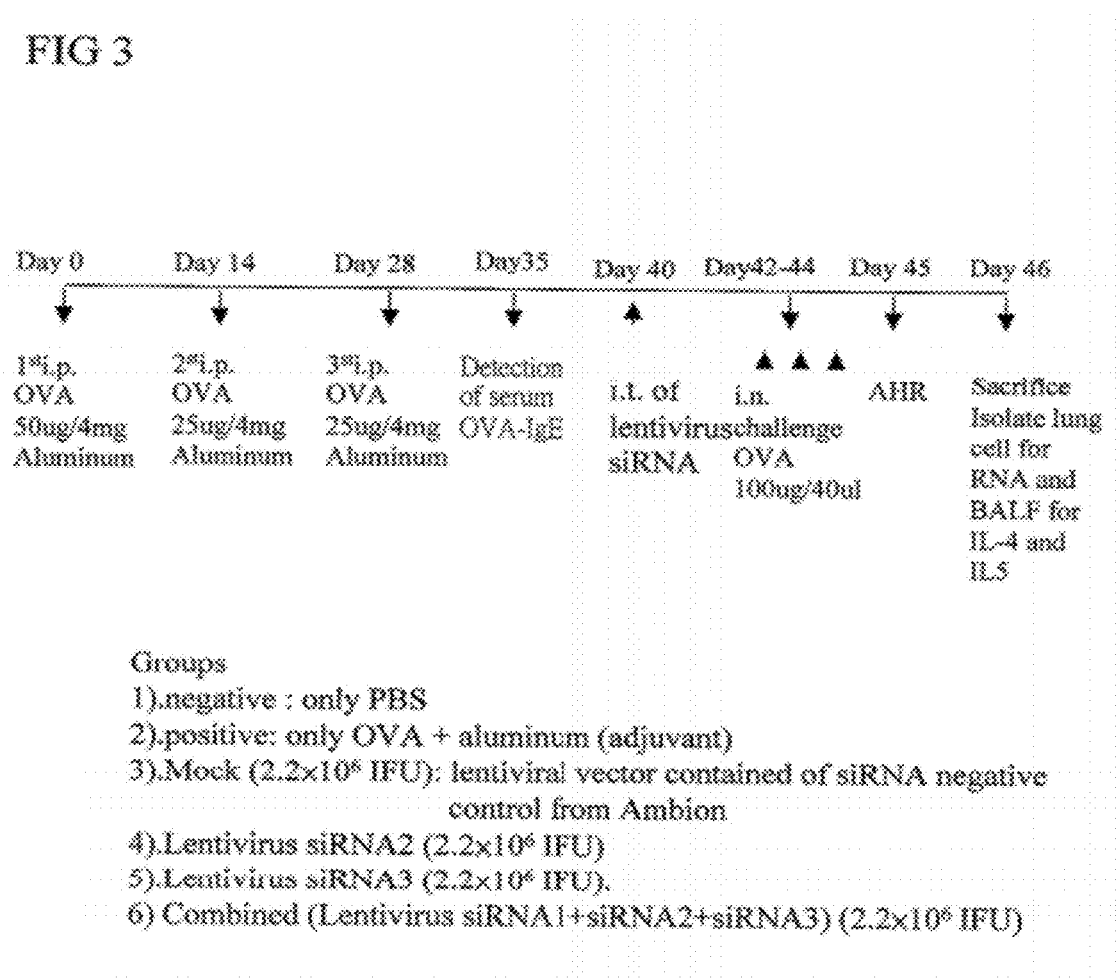
FIG. 3 illustrates the timeline of the OVA protocol used in accordance with one preferred embodiment of this invention for establishing the murine model of asthma.

Murine Model of Asthma Female BALB/c mice were purchased from and maintained in the Animal Center of the College of Medicine of National Taiwan University (Taiwan, R.O.C.). Animals were used between 6 and 10 weeks of age and were age matched within each experiment. Animal experiment protocol was approved by Animal Committee of the College of Medicine of National Taiwan University (Taiwan, R.O.C.) and briefly described as follows. On day 0, mice were sensitized by an intraperitoneal (i.p.) injection of 50 μg Ovalbumin (OVA) (Grade V, Sigma chemical co., St. Louis, Mo.) emulsified in 4 mg of aluminum hydroxide (Alumlmuject; Pierce Chemical, Rockford, Ill.) in a total volume of 200 μl. All mice were boosted with another shot of 25 μg OVA emulsified in 4 mg of aluminum hydroxide on day 14 and day 28, respectively. The mice in the negative control group were injected with phosphate buffer solution (PBS). On day 35, serum OVA-IgE of each animal was measured. Lentivirus siRNAs of Example 3.1 (including siRNA1, siRNA2 and siRNA3; $2.2 \times 10^6$ IFU each) were delivered intratracheally (i.t.) into anaesthetized animals on day 40, followed by OVA (100 μg) challenge intranasally on days 42 to 44. A mock virus (negative control siRNA lentiviral vector) or normal saline was used as a control. The $1 \times 10^5$ PFU of lentivirus was chosen by preliminary titration data (data not shown). For intratracheal injection, viruses in 50 μl of normal saline solution were injected with a catheter fitted with 0.61 mm (OD) of polyethylene tubing. Airway hyper-responsiveness (AHR) of each animal was measured on day 45, and all mice were bled and sacrificed on day 46 to end the experiment, and lung cells were isolated for further analysis including measurements of cell profiles and cytokines levels in brochoalveolar lavarge fluids (BALF). FIG. 3 illustrated the timeline of the above-identified protocol used in this study.

Measurements of OVA-specific IgE, IgG1, and $IgG_{2a}$ OVA-specific IgE and IgG1 (indicative of Th2 response) and $IgG_{2a}$ (indicative of Th1 response) were measured by sandwiched-ELISA as previously described (Lee et al., "Construction of single chain interleikun 12 plasmid to treat airway hyperresponsiveness in an animal model of asthma", Human Gene Therapy (2001) 12:2065-2079). 2 μg/ml OVA was coated to ELISA plates and incubated at 4° C. overnight. ELISA plates were washed with PBS containing 0.05% Tween 20, and diluted serum (10-fold dilution for OVA-specific IgE antibodies and 100-fold dilution for OVA-specific IgG1 and $IgG_{2a}$ determination) was added to the plates and incubated at room temperature for 2 hours. Biotin-conjugated anti-IgE, anti-IgG1, and anti-$IgG_{2a}$ antibodies and alkaline phosphatase conjugated avidin (Sigma, St. Louis, Mich. USA) were added subsequently. Enzyme activity was evaluated using TMB buffer (KPL Gaithersburg, Mich. USA) as the substrate and read using an enzyme-linked immunosorbent assay (ELISA) reader (MRX-TC; Dynex Technology, Chantilly, Va. USA). Readings at 450 nm were converted to nanograms per milliliter by using values obtained from standard curves. Standard curves were obtained from series dilution of known concentrations of purified mouse IgE, IgG1, and $IgG_{2a}$ (Pharmingen, San Diego, Calif.). Results were illustrated in FIG. 4. It is clear that comparable levels of all OVA-specific antibodies including IgE, IgG1, and $IgG_{2a}$ were induced upon treatment with siRNAs, either alone or in combination, as compared with that of the positive control.

Figure 5:
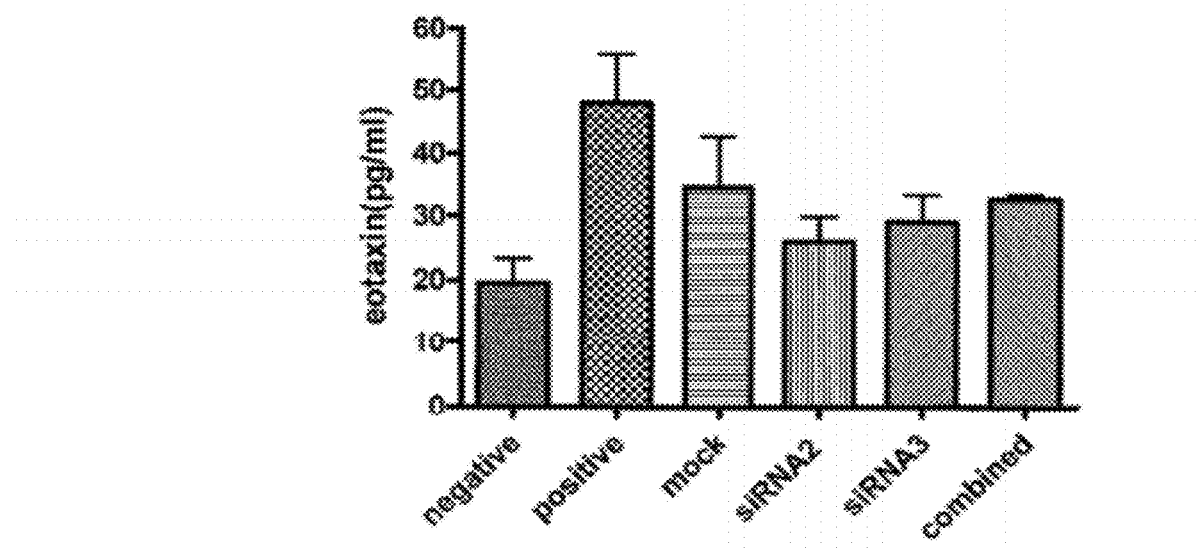
FIG. 5 illustrates the level of eotaxin in BAL fluid of mice of Example 3.2 as measured by ELISA.

Measurement of Cytokines The level of cytokines in BALF collected from the animals of Example 3.2 was detected by ELISA assay according to procedures described in Example 2. Results were illustrated in FIG. 5. The level of eotaxin in animals that had been treated with gata-3 siNA2 or gata-3 siNA3, either alone or in combination, was significantly lower than that of the animals in positive control group (FIG. 5).

Figure 6:
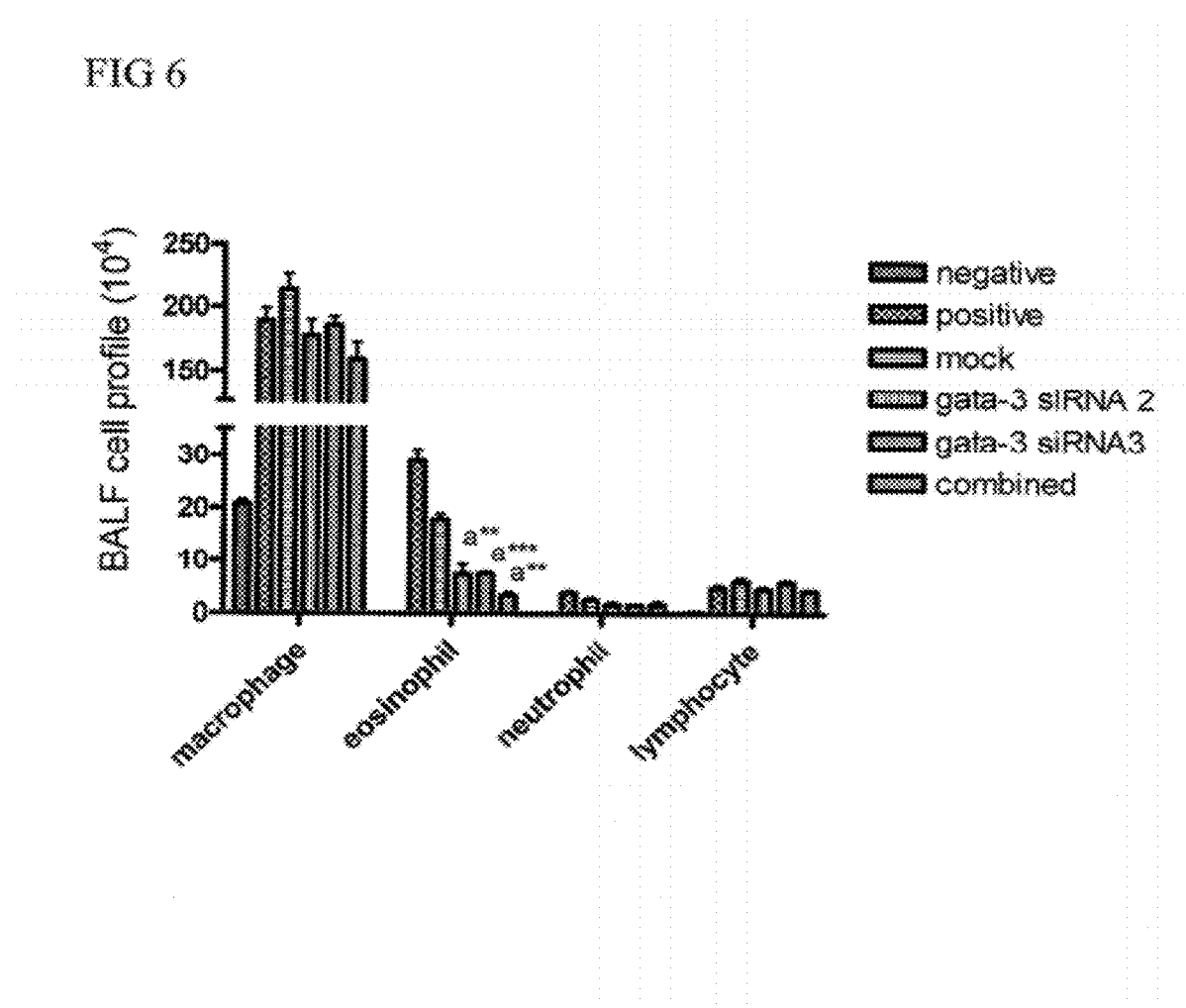
FIG. 6 illustrates the cell profiles in BALF collected from the mice in accordance with one embodiment of this invention. Total cell counts were determined on 1 ml HBSS, and data were expressed as mean±SEM, a $p<0.01$, a* $p<0.001$ as compared with the saline group.

Measurement of Cell Profiles in BALF Cell profiles including macrophages, eosinophils, neutrophils and lymphocytes in BALF collected from the animals of Example 3.2 were confirmed by Liu staining (Lee et al., "Administration of IL-12 exerts therapeutic instead of longterm preventive effect on Der p1 allergen-induced animal model of airway inflammation". (1999) Immunology 97: 232-240.), and results were illustrated in FIG. 6. Animals that had been treated with gata-3 siRNA2 or gata-3 siRNA3, either alone or in combination, showed significantly reduced number of eosinophils, indicating that siRNAs of Example 3.1 had successfully suppressed the activation of eosinophils, which are an indicative of inflammation.

Measurement of AHR AHR was measured in unrestrained animals by (barometric whole body plethysmography (Buxco, Troy, N.Y. USA). Briefly, mice were placed in the main chamber, and baseline readings were taken and averaged for 3 min. Aerosolized PBS or methacholine (MCh) in increasing concentration (3.125 to 25 mg/ml) were nebulized through an inlet of the main chamber for 3 min, and readings were taken and averaged for 3 min after each nebulization. Recordings of every 10 breaths are extrapolated to define the respiratory in breaths per minute. Airway reactivity was expressed as an enhanced pause (Penh) and data were expressed as the ratio of $Penh_{MCh}$ values compared with $Penh_{PBS}$ from three independent experiments according to procedures described by Hogan et al., "Aeroallergen-induced eosinophilic inflammation, lung damages and airway hyper-reactivity in mice can occur independently of IL-4 and allergen-specific immunoglobulins", (1997) J. Clin, Invest. 99:1329-1339.

Figure 7:
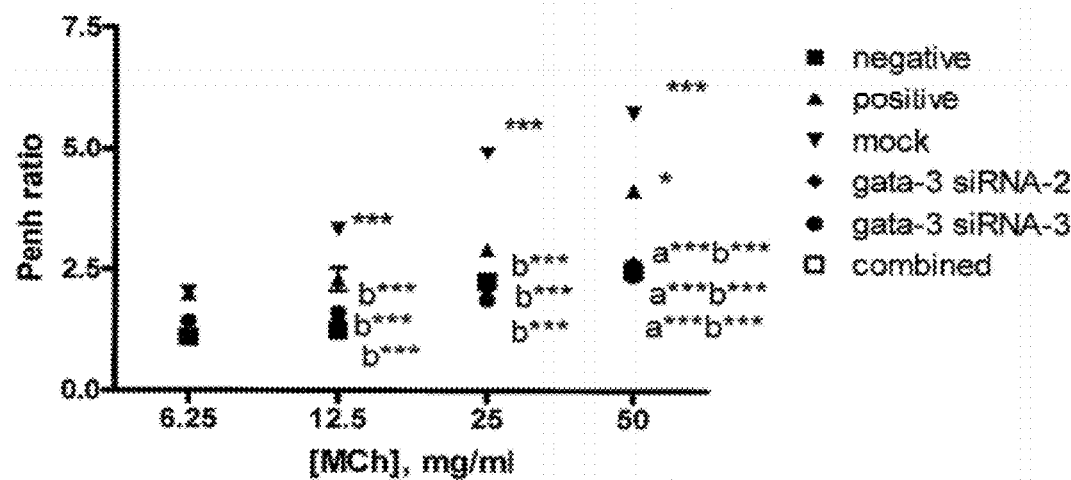
FIG. 7 illustrates the suppression of Mch-induced airway responsiveness by gata-3 siRNAs in OVA-sensitized mice in accordance with one preferred embodiment of this invention. AHR was measured by whole body plethysmography, and data were expressed as mean±SEM of the Penh values in the ratio of Penh values after PBS nebulization of 3 independent experiments. *$P<0.05$, *$P<0.001$ as compared with the negative group, a* $p<0.001$, as compared with respective positive groups, b*** $p<0.001$, as compared with respective mock groups.

Results were illustrated in FIG. 7. It is found that Mch-induced AHR was significantly reduced in animals treated with siRNA1, siRNA2 or siRNA3, as compared with that of the control animals, further confirmed that inhibition of the expression of IL-5 and eotaxin gene is effective in counteracting allergy-related symptoms.

Example 4

Suppressing the Expression of IL-5 and Eotaxin by Murine RNAi

Target sequences for IL-5 RNAi and eotaxin RNAi were selected and synthesized according to similar procedures described in Example 1. In particularly, three target sequences of IL-5 were chosen for producing murine IL-5 siRNAs, including siRNA4, using target sequence at position 263-283: AAGAATCAAACTGTCCGTGGG (SEQ ID NO: 4); siRNA5, using target sequence at position 636-656: AAGAAATTCCTGTAGCGCAGG (SEQ ID NO: 5); and siRNA6, using target sequence at position 1166-1186: AATCAGACTGTGCCATGACTG (SEQ ID NO: 6). Three target sequences of eotaxin were chosen and used for producing murine eotaxin siRNAs, including siRNA7, using target sequence at position 134-152: CTTCCTGCTGCTTTATCAT (SEQ ID NO: 7); siRNA8, using target sequence at position 282-294: GTGGGTCCAGGATGCCACA (SEQ ID NO: 8); and siRNA9, using target sequence at position 583-595: CACAATGGGACGAGTTAGG (SEQ ID NO: 9).

Figure 8:
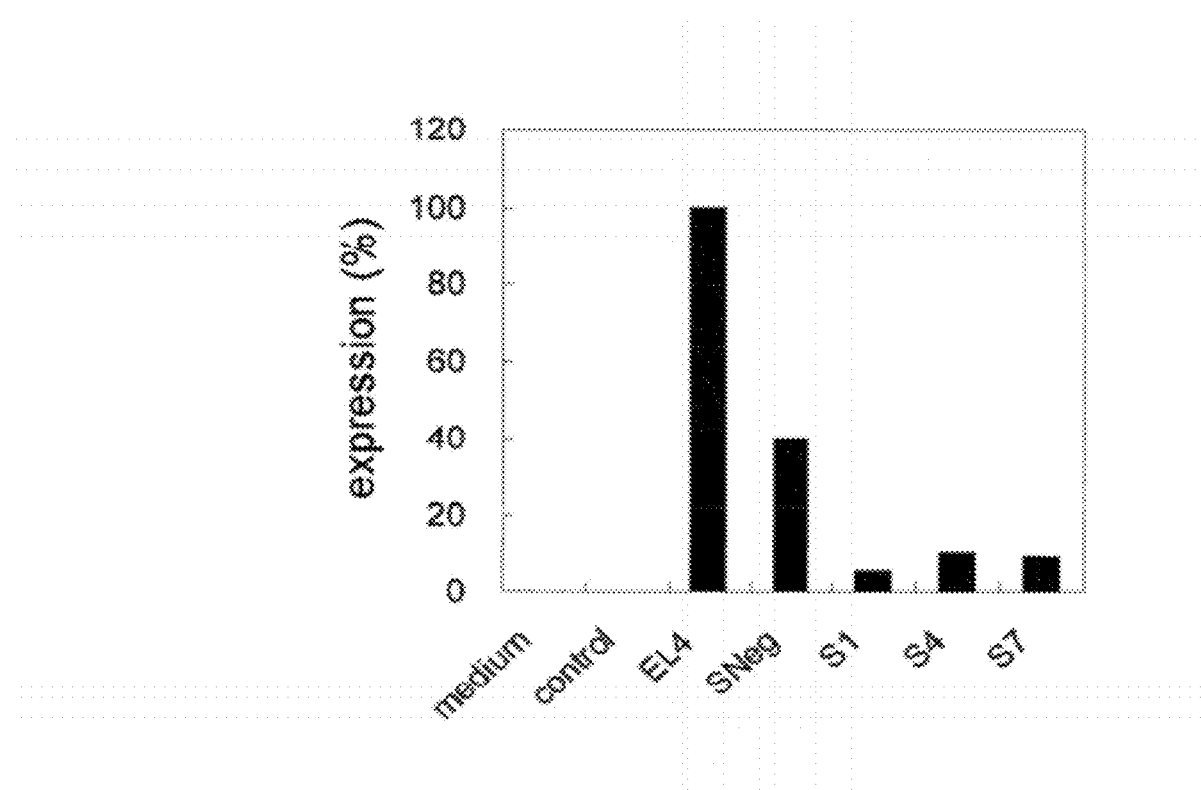
FIG. 8 illustrates the reduction of IL-5 expression after the transduction of IL-5 siRNAs in EL-4 cells that were treated with a combination of PMA (5 ng/ml) and cAMP (500 mM) for 24 hrs, detection of the expressed IL-5 was confirmed by ELISA. In the figure, "EL-4" refers to EL-4 cells treated with PMA and cAMP; "SNeg" refers to EL-4 cells transfected with pSECNeg containing a siRNA fragment non-relative to any genes of mice; "S1, S4 and S7" refer to EL-4 cells transfected with vectors containing siRNA4, siRNA5 and siRNA6, respectively.

Suppression of the IL-5 expression by the selected murine siRNAs (i.e., siRNA4, siRNA5 and siRNA6) in EL-4 cells were detected by ELISA in accordance with the procedures described in Example 2, and result was depicted in FIG. 8. The IL-5 expression was significantly suppressed by either one of the synthesized murine siNAs.

Similarly, the suppression of eotaxin expression by siRNAs (i.e., siRNA7, siRNA8 and siRNA9) were depicted in FIG. 9. Briefly, primary lung cells of BALB/C female mice were prepared and cultured in 48-well plates and incubated at 37° C. The cultured lung cells were then transfected with vectors containing eotaxin siRNAs, and the expressed eotaxin was detected by ELISA. Results showed that eotaxin/IL4 expression were both inhibited significantly by the selected synthesized murine eotaxin siRNAs.

The siRNAs directed to IL-5 RNAi and eotaxin RNAi were cloned into Lentiviral Vectors according to procedures of Example 3.1, and then were applied to Murine Model of Asthma of Example 3.2 in a similar manner and AHR, cell populations in BALF and cytokine levels were measured according to procedures described in Example 3.2. Results were illustrated in FIGS. 10-13.

Figure 10:
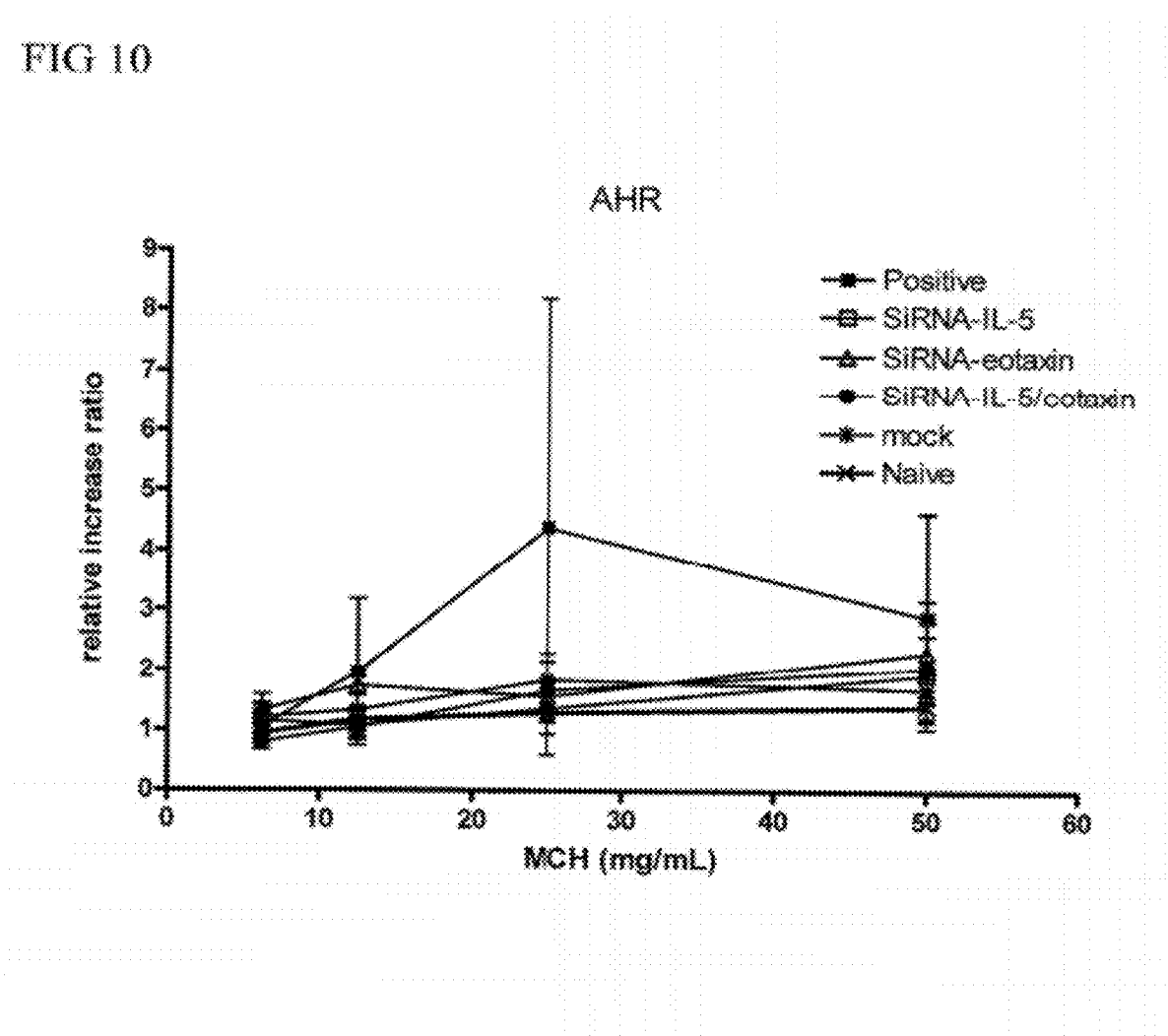
FIG. 10 illustrates the suppression of Mch-induced airway responsiveness by IL-5 siRNAs and/or eotaxin siRNAs in OVA-sensitized mite in accordance with one preferred embodiment of this invention. AHR was measured by whole body plethysmography.
Figure 13:
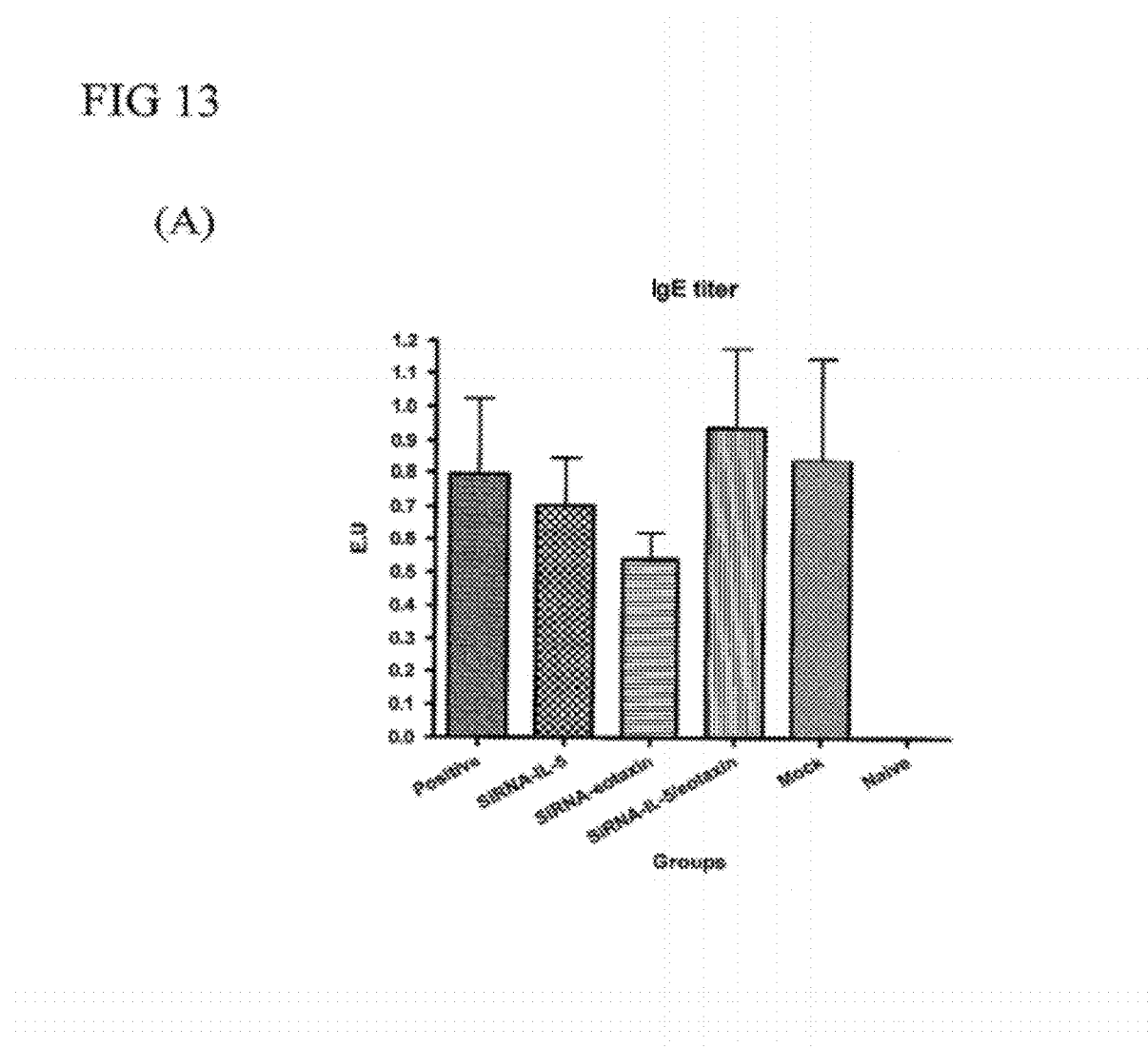
FIG. 13 are the bar diagrams showing the level of serum OVA-specific antibodies including (A) IgE, (B) IgG1 and (C) $IgG_{2a}$ in BALB/c mice treated with IL-5 and/or eotaxin siRNAs in accordance with one embodiment of this invention.

FIG. 10 illustrated the airway hyperresponsiveness by IL-5/eotaxin siRNAs. FIG. 11 illustrated the cell populations including monocytes (FIG. 11A), neutophils (FIG. 11B), lymphocytes (FIG. 11C) and eosinophils (FIG. 11D) in BALF collected from the animals pre-treated with IL-5/eotaxin siRNAs. FIG. 12 illustrated the concentration of cytokines including IL-5 (FIG. 12A) and eotaxin (FIG. 12B) in BALF collected from the animals pre-treated with IL-5/eotaxin siRNAs. FIG. 13 showed the serum level of OVA-specific antibodies including IgE, IgG1, and $IgG_{2a}$ in animals pre-treated with IL-5/eotaxin siRNAs.

Example 5

Isolation of Murine siRNAs for IL-4 and IL-13 RNAi and their Uses in Suppressing Airway Inflammation Target sequences for IL-4 RNAi and IL-13 RNAi were selected and used to produce siRNAs according to similar procedures described in Example 1. In particularly, three IL-4 sequences were used for producing murine siRNAs, including siRNA10, using target sequence at position 336-356: AAGCTGCACCATGAATGAGTC (SEQ ID NO: 10); siRNA11, using target sequence at position 181-201: AACACCACAGAGAGTGAGCTC (SEQ ID NO: 11); and siRNA12, using target sequence at position 47-67: AATGTACCAGGAGCCATATCC (SEQ ID NO: 12). Three murine siRNAs for IL-13 were synthesized, including siRNA13, using target sequence at position 238-258: AATGCCATCTACAGGACCCAG (SEQ ID NO: 13); siRNA14, using target sequence at position 154-174: AACGGCAGCATGGTATGGAGT (SEQ ID NO: 14); and siRNA15, using target sequence at position 100-120: AAGGAGCTTATTGAGGAGCTG (SEQ ID NO: 15).

The isolated murine IL-4 and/or IL-13 siRNAs were tested in similar manners as described above, and results confirmed that these isolated murine IL-4 and/or IL-13 siRNAs are effective in inhibiting IL-4 and/or IL-13 gene expression, as well as in counteracting allergy-related symptoms (results not shown).

Example 6

Dosage Effects of Murin siRNA in Suppressing Airway Inflammation

Murine siRNA, particularly siRNA5 (with sequence complementary to RNA sequence encoded by SEQ ID NO.: 5), was cloned into Lentivirus in according to procedures of Example 3.1, and three dosages including high ($3 \times 10^6$ IFU/mice), medium ($1.5 \times 10^6$ IFU/mice) and low ($3 \times 10^5$ IFU/mice) dose of the viral vectors containing siRNA5 were applied to Murine Model of Asthma of Example 3.2, respectively; and AHR, cell populations in BALF, cytokine levels and serum antibodies levels were measured according to procedures described in Example 3.2. Results were illustrated in FIGS. 14-17.

Figure 14:
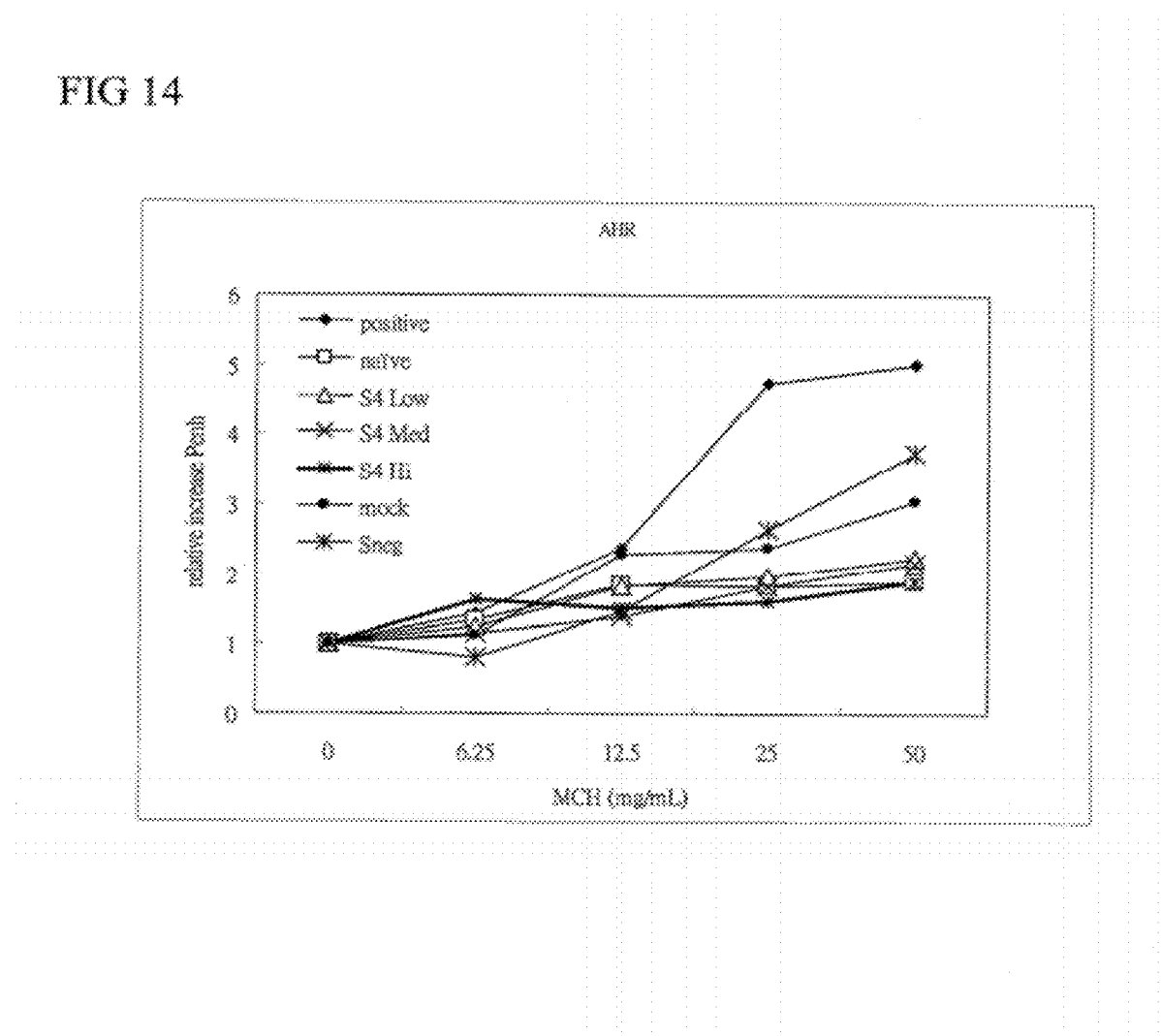
FIG. 14 illustrates the suppression of Mch-induced airway responsiveness by either high, medium or low dose of siRNA5 in OVA-sensitized mice in accordance with one preferred embodiment of this invention. AHR was measured by whole body plethysmography. In the figure, "S4 Low" refers to animals treated with low dose of siRNA5 ($3\times10^5$ IFU/mice), "S4 Med" refers to animals treated with medium dose of siRNA5 ($1.5\times10^6$ IFU/mice) and "S4 Hi" refers to animals treated with high dose of siRNA5 ($3\times10^6$ IFU/mice); "SNeg" refers to animals transfected with pSECNeg containing a siRNA fragment non-relative to any genes of mice.
Figure 15:
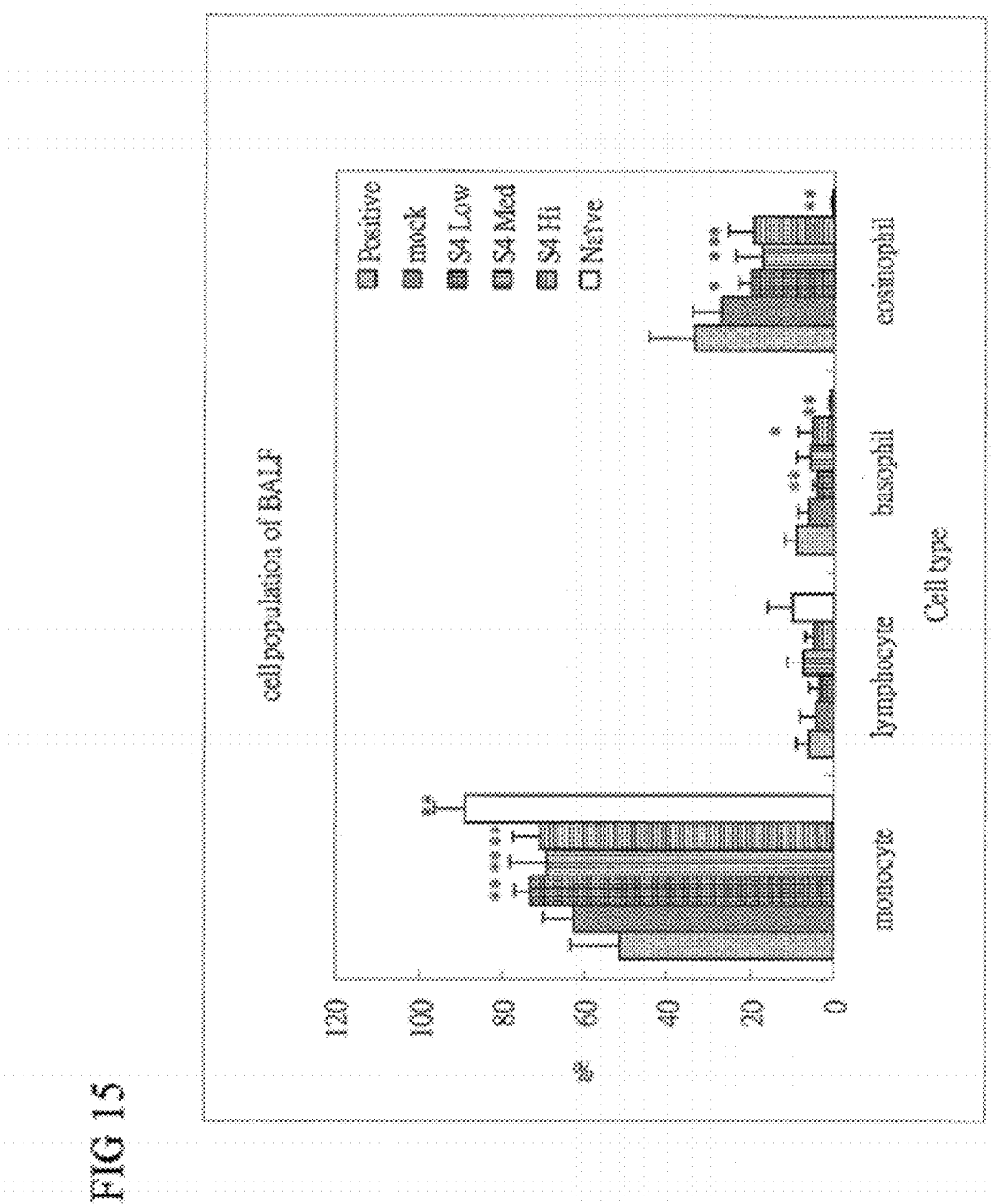
FIG. 15 illustrates the cell profiles including monocytes, lymphocytes, basophils and eosinophils in BALF collected from the mice of Example 5, which were treated with high, medium or low dosage of siRNA5, respectively. Total cell counts were determined on 1 ml HBSS, and data were expressed as mean±SEM, *p<0.01, ** p<0.001, as compared with the control group.
Figure 16:
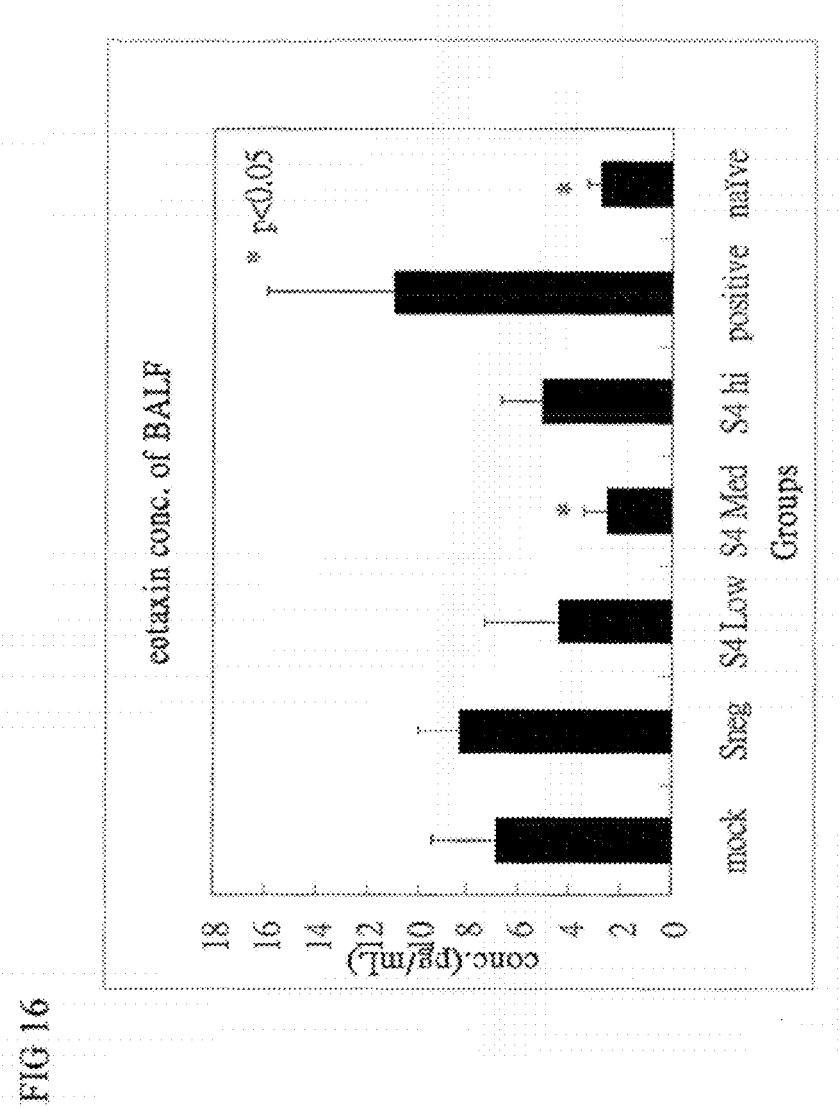
FIG. 16 illustrates the level of eotaxin concentration in BAL fluid of mice of Example 5, which were treated with high, medium or low dosage of siRNA5, respectively. Data were expressed as mean±SEM, *p<0.01, as compared with the control group.

FIG. 14 illustrated the dosage effects of murine siRNA5 in airway hyperresponsiveness. FIG. 15 illustrated the cell populations including monocytes, lymphocytes, basophils and eosinophils in BALF collected from the animals pre-treated with high, medium and low dose of siRNA5, respectively. FIG. 16 illustrated the concentration of eotaxin in BALF collected from the animals pre-treated with high, medium and low dose of siRNA5, respectively. FIG. 17 showed the serum level of OVA-specific antibodies including IgE, IgG1, and $IgG_{2a}$ in animals pre-treated with high, medium and low dose of siRNA5, respectively. Results indicated that all chosen dosages of murine siRNA5 were effective in counteracting allergy-related symptoms, with medium dose of siRNA5 being the preferred dosage expressing most significantly effects.

Construction of Human siRNAs and their Uses in Suppressing Airway Inflammation

Example 7

Figure 18:
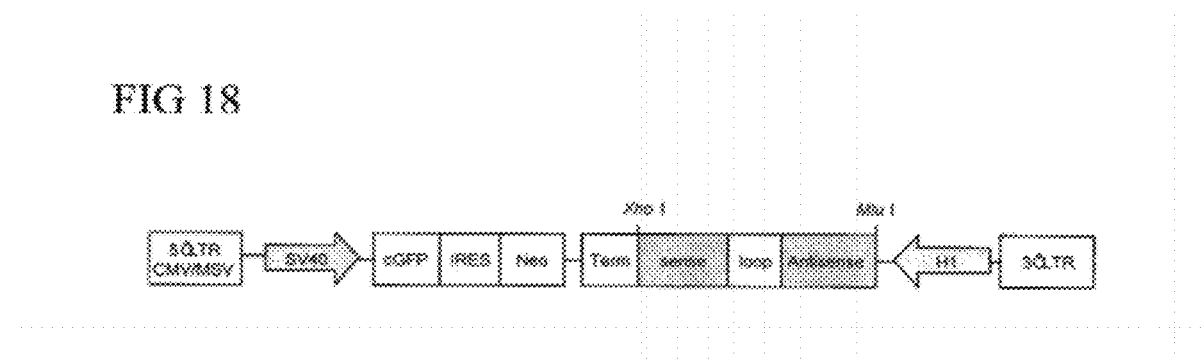
FIG. 18 is a schematic drawings of a human siRNA vector, in which a small DNA insert encoding a short hairpin RNA targeting a desired human gene may be cloned into this vector between Mlu I and Xho I sites, and used H1 promoter for siRNA expression; this vector also contains the coral GPF (cGFP) as a reporter gene and neomycin resistance gene for selection.

Isolation of Human siRNAs 7.1 Construction of Human siRNAs Expression Vectors Target sequences for human RNAi were selected and used to produce siRNAs according to similar procedures described in Example 1, except human siRNAs were cloned into pRNAT-H1.1/Retro (SD1255, GenScript, NJ, USA) plasmids (FIG. 18) and these human siRNA-expressing plasmids were transfected into A549 cells (a human alveolar basal epithelial cell line) or BEAS-2B cells (a human bronchial epithelial cell Line) by lipofectamine (Invirogen, Gaithersburg, Md.), and at 48 hrs after transfection, G418 (500 µg/ml) were added for 14 days for selection. For example, three IL-5 sequences were used for producing human siRNAs, including siRNA19, using target sequence at position 196-216: GGATTCCTGT-TCCTGTACATA (SEQ ID NO: 34); siRNA20, using target sequence at position 328-348: AGAAATACATTGACGGC-CAAA (SEQ ID NO: 35); and siRNA21, using target sequence at position 457-477: CTGGTTTGTTGCAGC-CAAAGA (SEQ ID NO: 36). The human siRNAs, including siRNA16~30 thus produced for gata-3, eotaxin, IL-4, IL-5, and IL-13, respectively, were provided in Table 2.

Figure 19:
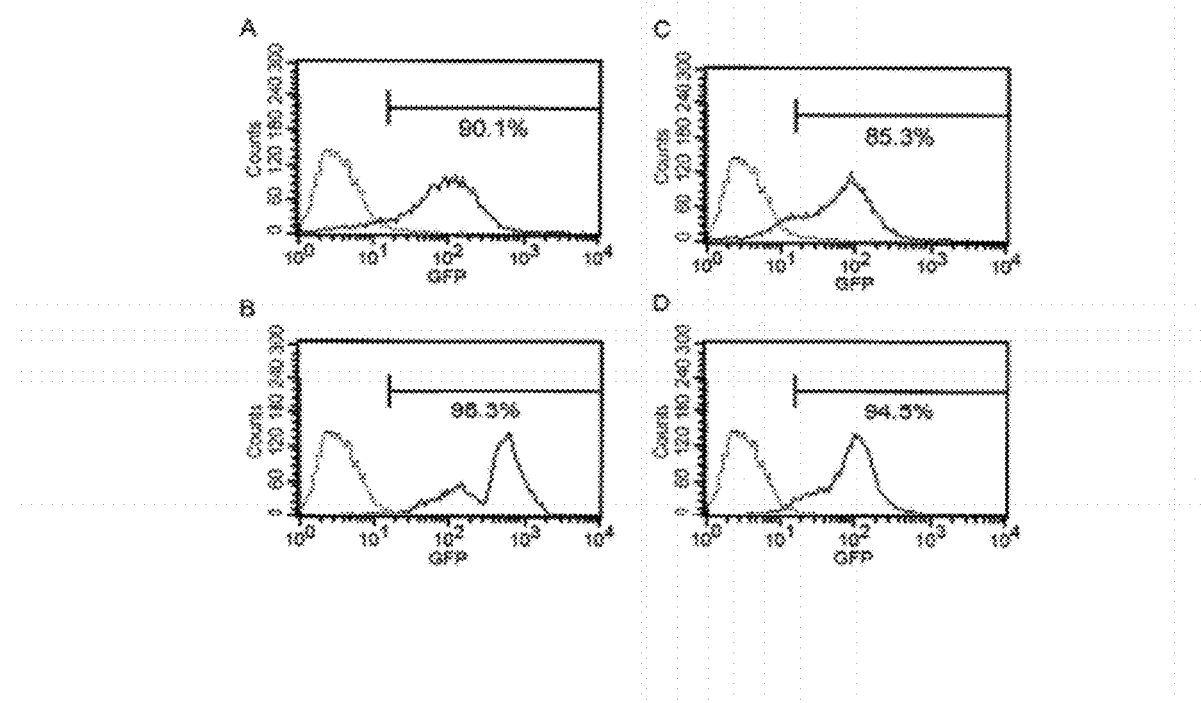
FIG. 19 illustrates the transfection efficiency of human siRNAs for eaotaxin-1 in BEAS-2B cells transfected with (A) empty, (B) siRNA 22, (C) siRNA 23 or (D) siRNA 24—containing vector by lipofectamine and selected by G418 (500 μg/ml) for 14 days. The frequency of transfected cells (GFP$^+$) were analyzed by FACS.

7.2 Real-Time Quantitative PCR mRNA were extracted from selected siRNA-expressing vector-transfected A549 cells using GeneStrips™ Hybridization Tubes (BNAture, Inc., CA, USA). cDNA synthesis was performed with random hexamer primers and SuperScript™ II RNase H⁻ reverse transcriptase. (Invitrogen, Gaithersburg, Md., USA) according to manufacturer's instructions. Quantitative real-time PCR was performed in an ABI PRISM 7700 cycler (Applied Biosystems, Foster City, Calif., USA) using the human IL-5 or eotaxin TaqMan gene expression assays (Applied Biosystems, Foster City, Calif., USA). All reported mRNA levels are normalized to the GAPDH mRNA level. As an example, the transfection efficiency of human siRNAs for eotaxin-1, including siRNA 22, 23 and 24, in BEAS-2B cells was illustrated in FIG. 19.

7.3 The Suppressing Efficiency of siRNA Targeting Human Eotaxin-1

Figure 20:
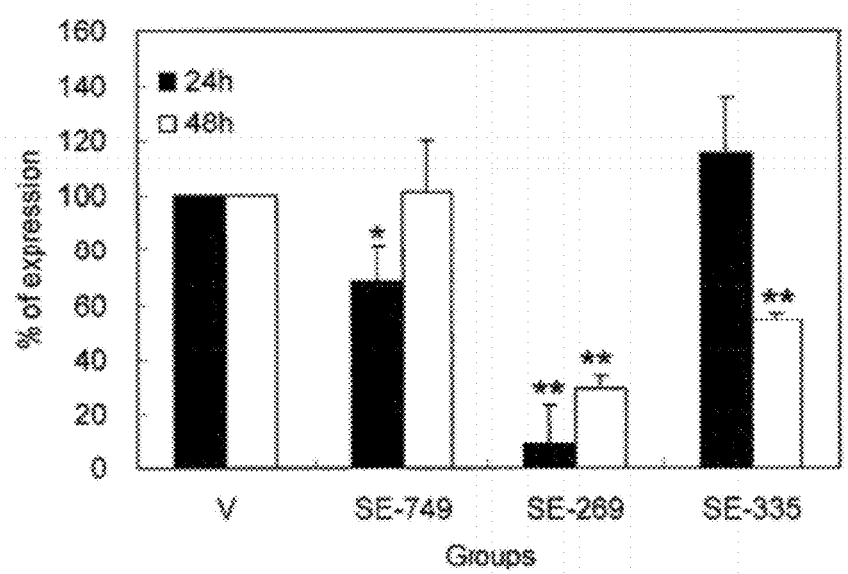
FIG. 20 illustrates the suppression efficiency of human siRNAs targeting eotaxin in BEAS-2B cells transfected with empty (V), siRNA 22 (SE-749-), siRNA 23 (SE-269), or siRNA 24 (SE-335)—containing vector, and stimulated with human TNF-α (50 ng/ml) and human IL-4 (50 ng/ml) for 24 hrs or 48 hrs, respectively. Eotaxin-1 expression of the control group (BEAS-2B cells transfected with empty vector) was taken as 100%. *, p<0.01 and **, p<0.001 compared with eotaxin-1 produced from the control group.

The virus-transformed human bronchial epithelium cell line BEAS-2B could secret eotaxin-1 with stimulation of human TNF-α and human IL-4. To investigate the suppression efficiency of siRNAs targeting human eotaxin-1, the siRNAs transfected BEAS-2B cells were stimulated with human TNF-α (50 ng/mL) and human IL-4 (50 ng/mL) for 24 hrs and 48 hrs, respectively. The concentration of eotaxin-1 in the supernatant was detected by ELISA. The suppression efficiency of human siRNAs targeting eaotaxin-1 in BEAS-2B cells is illustrated in FIG. 20. At 24 hrs after stimulation, the production of eotaxin-1 in siRNA23-transfected BEAS-2B cells reduced to a low level of 9±14%, compared with that of control cells (i.e., BEAS-2B cells transfected with empty vector). At 48 hrs after stimulation, the production of eotaxin-1 from either siRNA23- or siRNA24-transfected BEAS-2B cells decreased to 29±4% or 55±3%, respectively, compared with that of the control group.

7.4 The Suppressing Efficiency of siRNA Targeting Human Gata-3, IL-4 or IL13

Figure 21:
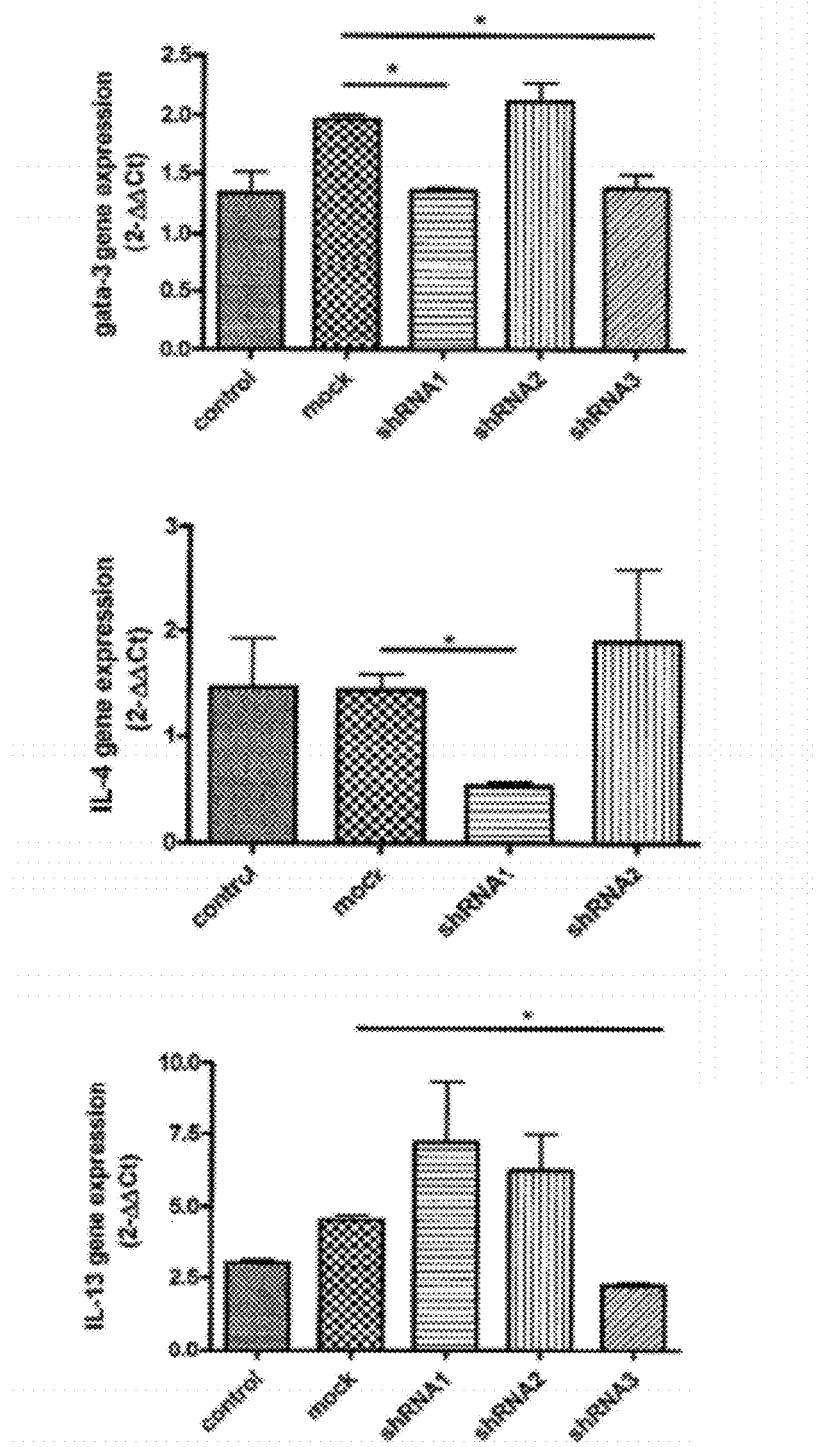
FIG. 21 illustrates the inhibitions of gata-3, IL-4 and IL-13 genes expression after transduction of shRNAs in Jurkat cells. $5\times10^5$ cells cultured in a 24-well dish, transfected with gata3, IL-4 or IL-13 shRNAs expressed pRNAin-H1.2/Retro plasmids for 4 hrs and treated with PMA (50 ng/ml) and PHA (1 μg/ml) for 48 hrs. Cells were transferred to a new 24-well dish, treated with PMA (50 ng/ml) and ionomycin (1 μg/ml) for 24 hrs, and then harvested the cells for RNA expression by realtime PCR. *p<0.05 as compared with respective groups.

Jurkat cells were transfected with human siRNAs constructed in accordance with the procedures described in Example 7.1, and the suppression efficiency of gata-3, IL-4 or IL-13 gene expression was monitored using real time PCR in according to the procedures described in Example 7.2. Results were illustrated in FIG. 21.

TABLE 1

The sequence of the selected target genes and murine siRNAs

| Target Gene | Position | Nucleic Acid Sequence (sense strand) | No. of siRNA | Ribonucleic Acid Sequence (sense strand) |
|---|---|---|---|---|
| Gata-3 | 316-336 | GAAGCTCAGTATCCGCTGACG (SEQ ID NO 1) | 1 | GAAGCUCAGUAUCCGCUGACG (SEQ ID NO 16) |
| | 1733-1753 | CCACTGAATCCGGATCCCATT (SEQ ID NO 2) | 2 | CCACUGAAUCCGGAUCCCAUU (SEQ ID NO 17) |
| | 1306-1324 | GATGTCTAGCAAATCGAAA (SEQ ID NO 3) | 3 | GAUGUCUAGCAAAUCGAAA (SEQ ID NO 18) |

TABLE 1-continued

The sequence of the selected target genes and murine siRNAs

| Target Gene | Position | Nucleic Acid Sequence (sense strand) | No. of siRNA | Ribonucleic Acid Sequence (sense strand) |
|---|---|---|---|---|
| IL-5 | 263-283 | AAGAATCAAACTGTCCGTGGG (SEQ ID NO 4) | 4 | AAGAAUCAAACUGUCCGUGGG (SEQ ID NO 19) |
| | 636-656 | AAGAAATTCCTGTAGCGCAGG (SEQ ID NO 5) | 5 | AAGAAAUUCCUGUAGCGCAGG (SEQ ID NO 20) |
| | 1166-1186 | AATCAGACTGTGCCATGACTG (SEQ ID NO 6) | 6 | AAUCAGACUGUGCCAUGACUG (SEQ ID NO 21) |
| eotaxin | 134-152 | CTTCCTGCTGCTTTATCAT (SEQ ID NO 7) | 7 | CUUCCUGCUGCUUUAUCAU (SEQ ID NO 22) |
| | 282-294 | GTGGGTCCAGGATGCCACA (SEQ ID NO 8) | 8 | GUGGGUCCAGGAUGCCACA (SEQ ID NO 23) |
| | 583-595 | CACAATGGGACGAGTTAGG (SEQ ID NO 9) | 9 | CACAAUGGGACGAGUUAGG (SEQ ID NO 24) |
| IL-4 | 47-67 | AAGCTGCACCATGAATGAGTC (SEQ ID NO 10) | 10 | AAGCUGCACCAUGAAUGAGUC (SEQ ID NO 25) |
| | 181-201 | AACACCACAGAGAGTGAGCTC (SEQ ID NO 11) | 11 | AACACCACAGAGAGUGAGCUC (SEQ ID NO 26) |
| | 336-356 | AATGTACCAGGAGCCATATCC (SEQ ID NO 12) | 12 | AAUGUACCAGGAGCCAUAUCC (SEQ ID NO 27) |
| IL-13 | 100-120 | AATGCCATCTACAGGACCCAG (SEQ ID NO 13) | 13 | AAUGCCAUCUACAGGACCCAG (SEQ ID NO 28) |
| | 154-174 | AACGGCAGCATGGTATGGAGT (SEQ ID NO 14) | 14 | AACGGCAGCAUGGUAUGGAGU (SEQ ID NO 29) |
| | 238-258 | AAGGAGCTTATTGAGGAGCTG (SEQ ID NO 15) | 15 | AAGGAGCUUAUUGAGGAGCUG (SEQ ID NO 30) |

TABLE 2

The sequence of the selected target genes and human siRNAs

| Target Gene | Position | Nucleic Acid Sequence (sense strand) | No. of siRNA | Ribonucleic Acid Sequence (sense strand) |
|---|---|---|---|---|
| Gata-3 | 537-557 | CGAGAAAGAGTGCCTCAAGTA (SEQ ID NO 31) | 16 | CGAGAAAGAGUGCCUCAAGUA (SEQ ID NO 46) |
| | 1080-1100 | CATCCAGACCAGAAACCGAAA (SEQ ID NO 32) | 17 | CAUCCAGACCAGAAACCGAAA (SEQ ID NO 47) |
| | 185-205 | CCTACTACGGAAACTCGGTCA (SEQ ID NO 33) | 18 | CCUACUACGGAAACUCGGUCA (SEQ ID NO 48) |
| IL-5 | 196-216 | GGATTCCTGTTCCTGTACATA (SEQ ID NO 34) | 19 | GGAUUCCUGUUCCUGUACAUA (SEQ ID NO 49) |
| | 328-348 | AGAAATACATTGACGGCCAAA (SEQ ID NO 35) | 20 | AGAAAUACAUUGACGGCCAAA (SEQ ID NO 50) |
| | 457-477 | CTGGTTTGTTGCAGCCAAAGA (SEQ ID NO 36) | 21 | CUGGUUUGUUGCAGCCAAAGA (SEQ ID NO 51) |
| eotaxin | 749-769 | TTGTAAAGGTCCTGGCAAAGA (SEQ ID NO 37) | 22 | UUGUAAAGGUCCUGGCAAAGA (SEQ ID NO 52) |
| | 269-289 | TTCAGCGACTAGAGAGCTACA (SEQ ID NO 38) | 23 | UUCAGCGACUAGAGAGCUACA (SEQ ID NO 53) |
| | 335-355 | AGACCAAACTGGCCAAGGATA (SEQ ID NO 39) | 24 | AGACCAAACUGGCCAAGGAUA (SEQ ID NO 54) |
| IL-4 | 133-153 | AAGAACACAACTGAGAAGGAA (SEQ ID NO 40) | 25 | AAGAACACAACUGAGAAGGAA (SEQ ID NO 55) |
| | 355-375 | AACTTCTTGGAAAGGCTAAAG (SEQ ID NO 41) | 26 | AAUUCUUGGAAAGGCUAAAG (SEQ ID NO 56) |
| | 87-107 | CACCTTACAGGAGATCATCAA (SEQ ID NO 42) | 27 | CACCUUACAGGAGAUCAUCAA (SEQ ID NO 57) |
| IL-13 | 389-409 | AGGACCTGCTCTTACATTTAA (SEQ ID NO 43) | 28 | AGGACCUGCUCUUACAUUUAA (SEQ ID NO 58) |
| | 137-157 | TCATTGAGGAGCTGGTCAACA (SEQ ID NO 44) | 29 | UCAUUGAGGAGCUGGUCAACA (SEQ ID NO 59) |
| | 431-451 | AGTTCAACCGAAACTTCGAAA (SEQ ID NO 45) | 30 | AGUUCAACCGAAACUUCGAAA (SEQ ID NO 60) |

INDUSTRIAL APPLICABILITY

It is an advantage of the present invention that it provides a novel solution for treating allergic diseases by use of siRNAs designed especially to counteract the expression of at least one gene related to airway inflammation, such as gata-3, IL-4, IL-5, IL-13 or eotaxin gene. The siRNAs, methods and compositions according to the present invention may increase immunity of a host to inhibit inflammation and control allergy and thereby provides treatment to a subject suffering from allergic diseases such as pollinosis, bronchial asthma, allergic rhinitis, sinusitis, respiratory distress syndrome, atopic dermatitis, and anaphylactic shock, by minimizing and/or alleviating airway inflammation of the subject.

The foregoing description of various embodiments of the invention has been presented for purpose of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An isolated double stranded short interfering ribonucleic acid (siRNA) molecule that directs cleavage of a gata-3 RNA via RNA interference, wherein (a) each strand of said siRNA molecule is about 19 to 21 ribonucleotides in length; and (b) one strand of said siRNA molecule is a ribonucleotide sequence complementary to the full length of SEQ ID No 48 to direct cleavage of the gata-3 RNA via RNA interference.

2. The siRNA molecule of claim 1 wherein said gata-3 RNA targeted by the siRNA molecule is of human origin.

3. The siRNA molecule of claim 1, wherein said siRNA molecule has a sense strand encoded by the full length of SEQ ID No 33.

4. A composition for treating allergy, comprising the siRNA molecule of claim 1, in a pharmaceutically acceptable carrier.

5. The composition of claim 4, wherein the allergy is pollinosis, bronchial asthma, sinusitis, respiratory distress syndrome or allergic rhinitis.

6. The composition of claim 4, wherein said gata-3 RNA targeted by the siRNA molecule is of human origin.

7. The composition of claim 6, wherein said siRNA molecule has a sense strand encoded by the full length of SEQ ID No 33.

* * * * *